(12) United States Patent
Babbar et al.

(10) Patent No.: US 12,161,703 B2
(45) Date of Patent: Dec. 10, 2024

(54) TRANSMUCOSAL BOTULINUM TOXIN COMPOSITIONS, KITS, AND METHODS FOR TREATING BLADDER DISORDERS

(71) Applicant: REVANCE THERAPEUTICS, INC., Newark, CA (US)

(72) Inventors: Sunita Babbar, Fremont, CA (US); Curtis L. Ruegg, Redwood City, CA (US)

(73) Assignee: REVANCE THERAPEUTICS, INC., Newark, CA (US)

( * ) Notice: Subject to any disclaimer, the term of this patent is extended or adjusted under 35 U.S.C. 154(b) by 290 days.

(21) Appl. No.: 16/643,320

(22) PCT Filed: Aug. 28, 2018

(86) PCT No.: PCT/US2018/048361
§ 371 (c)(1),
(2) Date: Feb. 28, 2020

(87) PCT Pub. No.: WO2019/046311
PCT Pub. Date: Mar. 7, 2019

(65) Prior Publication Data
US 2021/0162026 A1 Jun. 3, 2021

Related U.S. Application Data

(60) Provisional application No. 62/550,850, filed on Aug. 28, 2017.

(51) Int. Cl.
| | | |
|---|---|---|
| *A61K 38/00* | (2006.01) | |
| *A61K 9/00* | (2006.01) | |
| *A61K 9/127* | (2006.01) | |
| *A61K 38/48* | (2006.01) | |
| *A61K 47/64* | (2017.01) | |
| *A61P 13/06* | (2006.01) | |

(52) U.S. Cl.
CPC ........ *A61K 38/4893* (2013.01); *A61K 9/0034* (2013.01); *A61K 9/127* (2013.01); *A61K 47/6455* (2017.08); *A61P 13/06* (2018.01); *C12Y 304/24069* (2013.01)

(58) Field of Classification Search
CPC ............ A61K 38/4893; A61K 47/6455; A61K 9/0034; A61K 9/127; A61P 13/06; A61P 13/10; C12Y 304/24069
See application file for complete search history.

(56) References Cited

U.S. PATENT DOCUMENTS

| | | | |
|---|---|---|---|
| 6,585,993 B2 | 7/2003 | Donovan | |
| 6,605,055 B1 * | 8/2003 | Sinofsky | A61B 18/24 604/101.02 |
| 7,270,826 B2 | 9/2007 | Borodic | |
| 7,335,367 B2 | 2/2008 | Borodic | |
| 7,459,164 B2 | 12/2008 | Borodic | |
| 7,537,773 B1 | 5/2009 | Borodic | |
| 7,670,608 B2 | 3/2010 | Borodic | |
| 7,807,780 B2 | 10/2010 | Waugh | |
| 8,092,788 B2 | 1/2012 | Dake | |
| 8,192,979 B2 | 6/2012 | Borodic | |
| 8,404,249 B2 | 3/2013 | Dake | |
| 8,580,317 B2 | 11/2013 | Waugh | |
| 8,623,811 B2 | 1/2014 | Stone | |
| 8,628,756 B2 | 1/2014 | Waugh | |
| 8,691,769 B2 | 4/2014 | Borodic | |
| 9,066,851 B2 | 6/2015 | Borodic | |
| 9,180,081 B2 | 11/2015 | Dake | |
| 9,393,291 B2 | 7/2016 | Borodic | |
| 9,469,849 B2 | 10/2016 | Ruegg | |
| 9,901,627 B2 | 2/2018 | Borodic | |
| 9,956,435 B2 * | 5/2018 | Ruegg | A61P 37/04 |
| 10,201,594 B2 | 2/2019 | Ruegg | |
| 2009/0304747 A1 | 12/2009 | Petrou | |
| 2010/0168023 A1 | 7/2010 | Ruegg | |
| 2010/0330123 A1 * | 12/2010 | Thompson | A61K 47/22 424/239.1 |

(Continued)

FOREIGN PATENT DOCUMENTS

WO 2013153550 4/2013

OTHER PUBLICATIONS

Chuang et al. 2014 (Bladder Instillation of Liposome Encapsulated OnabotulinumtoxinA Improves Overactive Bladder Symptoms: A Prospective, Multicenter, Double-Blind Randomized Trial; The Journal of Urology 192: 1743-1749). (Year: 2014).*
Lee et al. 'Mechanism of Action of Onabotulinumtoxina on Lower Urinary Tract Dysfunction' 2014, Tzu Chi Medical Journal, vol. 26, No. 1, pp. 1-4.
International Search Report from PCT/US2018/48361, pp. 1-4, Nov. 26, 2018.
Written Opinion from PCT/US2018/48361, pp. 1-6, Nov. 26, 2018.
European Search Report from corresponding European application No. 18851805.4, pp. 1-8, Nov. 26, 2018.
Brubaker et al., Refractory Idiopathic Urge Urinary Incontinence and Botulinum A Injection, J. Urol. Jul. 2008; 180 (1): 217-222.

(Continued)

*Primary Examiner* — Mary Maille Lyons
(74) *Attorney, Agent, or Firm* — Ballard Spahr LLP

(57) ABSTRACT

The present invention provides methods, compositions, and kits for treating bladder disorders or conditions, in which botulinum toxin is topically administered to the mucosal inner lining or urothelium of the bladder, of a subject in need thereof, for transmucosal delivery across the urothelium to surrounding bladder wall musculature and/or neuronal tissue. Rather than requiring injection, the toxin instead may be administered by instillation in solution via the urethra. In particular, the botulinum toxin is administered in conjunction with a positively charged or lipophilic carrier comprising a positively charged polymeric backbone or a hydrophobic backbone with covalently attached groups that enhance transmucosal transport across the urothelium and may also stabilize the botulinum toxin in aqueous formulations.

31 Claims, 4 Drawing Sheets

Specification includes a Sequence Listing.

(56) References Cited

U.S. PATENT DOCUMENTS

| | | | |
|---|---|---|---|
| 2013/0129699 A1* | 5/2013 | Gaylis | A61P 43/00 |
| | | | 424/94.2 |
| 2013/0202636 A1* | 8/2013 | Dake | A61K 39/08 |
| | | | 424/197.11 |
| 2014/0056811 A1* | 2/2014 | Jacob | C07K 14/47 |
| | | | 424/193.1 |
| 2014/0120077 A1 | 5/2014 | Ruegg | |
| 2014/0154237 A1 | 6/2014 | Waugh | |
| 2016/0095908 A1 | 4/2016 | Borodic | |
| 2017/0136105 A1 | 5/2017 | Ho | |
| 2018/0311333 A1 | 11/2018 | Ruegg | |
| 2020/0179498 A1 | 6/2020 | Ruegg | |
| 2020/0384090 A1 | 12/2020 | Rubio | |
| 2020/0390871 A1 | 12/2020 | Rubio | |
| 2021/0162026 A1 | 6/2021 | Babbar | |
| 2023/0210963 A1 | 7/2023 | Chehrenama | |

OTHER PUBLICATIONS

Pearce, L. Bruce, et al. "Measurement of botulinum toxin activity: evaluation of the lethality assay." Toxicology and Applied Pharmacology 128.1 (1994): 69-77.

Hoffman, Robert O., and Eugene M. Helveston. "Botulinum in the treatment of adult motility disorders." International ophthalmology clinics 26.4 (1986): 241-250.

Kessler, Horst. "Peptoids—a new approach to the development of pharmaceuticals." Angewandte Chemie International Edition in English 32.4 (1993): 543-544.

Zuckermann, Ronald N., et al. "Efficient method for the preparation of peptoids [oligo (N-substituted glycines)] by submonomer solid-phase synthesis." Journal of the American Chemical Society 114.26 (1992): 10646-10647.

Simon, Reyna J., et al. "Peptoids: a modular approach to drug discovery." Proceedings of the National Academy of Sciences 89.20 (1992): 9367-9371.

* cited by examiner

TRANSMUCOSAL BOTULINUM TOXIN COMPOSITIONS, KITS, AND METHODS FOR TREATING BLADDER DISORDERS

CROSS-REFERENCE TO RELATED APPLICATIONS

This application is a national stage filing under 35 U.S.C. § 371 of International Application No. PCT/US2018/048361, filed on Aug. 28, 2018, which claims benefit of priority under 35 U.S.C. 119 to Provisional Patent Application No. 62/550,850, filed Aug. 28, 2017, the contents of both applications are incorporated herein by reference in their entireties.

SEQUENCE LISTING

The instant application contains a Sequence Listing which has been submitted electronically in ASCII format and is hereby incorporated by reference in its entirety. Said ASCII copy, created on Feb. 11, 2021, is named 13720_0027_SL.txt and is 16,406 bytes in size.

RELATED FIELDS

The compositions, kits, and methods described herein generally relate to the fields of medical treatments involving botulinum toxin. More specifically, methods and kits are provided for transmucosally delivering compositions comprising botulinum toxin to cells and tissues of the luminal bladder wall for treating bladder disorders without the need to inject the toxin, thereby alleviating discomfort and side effects of injection. The transmucosal botulinum toxin compositions, kits, and methods are especially applicable to the treatment of overactive bladder.

BACKGROUND

Overactive bladder (OAB) is the most common type of bladder disorder that afflicts patients and causes significant discomfort. OAB sufferers experience an urgent need to urinate, as well as an involuntary loss of urine. The disorder has a profoundly negative impact on the quality of life of millions of people. It is estimated that in the United States alone, over 39 million people suffer from OAB, and the condition affects about 200 million people worldwide.

While medications that relax the bladder and reduce episodes of urge and/or incontinence are treatment options, they are ineffective in about 50% of OAB cases and can have significant side effects. Examples of such medications include Tolterodine (Detrol). (Ditropan XL), Oxybutynin, Trospium (Sanctura), Solifenacin (Vesicare), Darifenacin (Enablex), Mirabegron (Myrbetriq) and Fesoterodine (Toviaz). Common side effects of most of these drugs include dry eyes and dry mouth; ironically, drinking water to quench thirst caused by the drugs can aggravate the symptoms of overactive bladder. Constipation is another potential side effect that can also aggravate the bladder symptoms.

In 2011, the FDA approved the use of botulinum toxin (Botox®) to treat OAB. However, Botox® treatment, commonly by injection, has a number of disadvantages. For example, the treatments are expensive and painful, often requiring 20-30 injections and typically requiring sedation, as well as posing risks such as urinary tract infections.

Botulinum toxins (also known as botulin toxins or botulinum neurotoxins) are neurotoxins produced by the gram-positive bacteria *Clostridium botulinum*. They act to produce paralysis of muscles by preventing synaptic transmission by inhibiting the release of acetylcholine across the neuromuscular junction and are thought to act in other ways as well. They essentially block signals that normally cause muscle spasms or contractions, resulting in paralysis.

Botulinum toxin is classified into eight serologically related but distinct neurotoxins. Of these, seven can cause paralysis, namely botulinum neurotoxin serotypes A, B, C, D, E, F and G. Each serotype is distinguished by neutralization with type-specific antibodies. Nonetheless, the molecular weight of the neuroactive botulinum toxin protein molecule, for all seven of these active botulinum toxin serotypes, is about 150 kDa. As released by the bacterium, the botulinum toxins are complexes comprising the 150 kDa botulinum toxin protein molecule associated with other non-toxin proteins. The botulinum toxin type A complex can be produced by the *Clostridia* bacterium as 900 kD, 500 kDa, and 300 kDa forms. Botulinum toxin types B and C are apparently produced as only a 700 kDa or 500 kDa complex. Botulinum toxin type D is produced as both 300 kDa and 500 kDa complexes. Botulinum toxin types E and F are produced as approximately 300 kDa complexes. The complexes having molecular weights greater than about 150 kD are believed to contain a non-toxin hemagglutinin protein and a non-toxin and non-toxic nonhemagglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. In addition, it is possible that the larger (greater than about 150 kD molecular weight) botulinum toxin complexes result in a slower rate of diffusion of the botulinum toxin away from a site of intramuscular injection of a botulinum toxin complex.

The different serotypes of botulinum toxin vary in the animal species they affect and in the severity and duration of paralysis they evoke. For example, it has been determined that botulinum toxin type A is 500 times more potent, as measured by the rate of paralysis produced in the rat, than is botulinum toxin type B. In addition, botulinum toxin type B has been determined to be non-toxic in primates at a dose of 480 U/kg, about 12 times the primate LD50 for type A. Due to the molecular size and structure of botulinum toxin, it cannot cross stratum corneum and the multiple layers of the underlying skin architecture.

Despite the potent toxicity of botulinum toxin of subtype A, the muscle-paralyzing effects of botulinum toxin have been used for therapeutic effects. Controlled administration of botulinum toxin, typically by injection, has been used to provide muscle paralysis to treat conditions, for example, neuromuscular disorders characterized by hyperactive skeletal muscles. Conditions that have been treated with botulinum toxin include hemifacial spasm, adult onset spasmodic torticollis, anal fissure, blepharospasm, cerebral palsy, cervical dystonia, migraine headaches, strabismus, temperomandibular joint disorder, and various types of muscle cramping and spasms. More recently, the muscle-paralyzing effects of botulinum toxin have been advantageous in cosmetic applications, such as treatment of wrinkles, frown lines, as well as other conditions caused by spasms or contractions of facial muscles.

With respect to treating bladder disorders, administration of botulinum toxin via a non-injectable route would provide a safer and more desirable alternative due to, for example, the painless nature of application, the larger treatment surface area that can be covered, the reduced training necessary for administration, the lack of a need for large wells of toxin to achieve therapeutic results, and the smaller doses needed to produce a desired effect. Thus, there remains a need in the art for more effective compositions and methods for administering botulinum toxin, such as via transmucosal delivery, as well as more effective methods of treating and/or preventing bladder disorders, for example, without requiring injections. The present invention meets these and other needs.

SUMMARY

The present invention provides methods, compositions, and kits for treating bladder disorders or conditions, in which botulinum toxin is topically administered to the mucosal inner lining or urothelium of the bladder, of a subject in need thereof, for transmucosal delivery across the urothelium to surrounding bladder wall musculature and/or neuronal tissue. Rather than requiring injection, the toxin instead may be administered by instillation in solution via the urethra. In particular embodiments, the botulinum toxin is administered in conjunction with a positively charged carrier comprising a positively charged polymeric backbone with covalently attached groups that enhance transmucosal transport across the urothelium and may also stabilize the botulinum toxin in aqueous formulations. In other embodiments, the botulinum toxin is administered in conjunction with a lipophilic carrier comprising a hydrophobic oligomeric or polymeric backbone with covalently attached groups that enhance transmucosal transport across the urothelium.

The positively charged or lipophilic carrier, for use in the methods, compositions, and kits of the invention, enables transmucosal delivery of botulinum toxin through the urothelium, without the need to inject the toxin, thereby avoiding the attendant unpleasant and uncomfortable side effects of injection. In particular embodiments, the methods, compositions, and kits deliver botulinum toxin through the mucosal inner layer of the bladder wall, following topical administration to the luminal surface by instillation of a solution comprising botulinum toxin. "Instillation," also termed herein as "bladder instillation" or "intravesical instillation," refers to delivery of a liquid or solution by any means to the lumen of the bladder, usually via a catheter introduced into the bladder via the urethra, allowing contact of the liquid or solution, e.g., a solution carrying botulinum toxin, with a portion or all of the luminal surface of the bladder to effect topical administration and transmucosal delivery.

One aspect of the invention thus provides a method of treating a bladder disorder or condition in a subject in need thereof, the method comprising administering to a luminal surface of the bladder of the subject an effective amount of a composition comprising a botulinum toxin in conjunction with a positively charged carrier, the carrier comprising a positively charged polymeric backbone having covalently attached thereto one or more positively charged efficiency groups, preferably where the toxin and the carrier associate to form a non-covalent complex. Generally, the botulinum toxin is not covalently linked to the carrier. In some embodiments, the positively charged polymeric backbone of the carrier directly associates non-covalently with the botulinum toxin. The composition serves to transmucosally deliver an effective amount of botulinum toxin following administration to the bladder luminal surface. In other embodiments, the method comprises administering to a luminal surface of the bladder of the subject an effective amount of a composition comprising a botulinum toxin in conjunction with a lipophilic carrier, the carrier comprising a hydrophobic oligomeric or polymeric backbone with covalently attached thereto one or more positively charged efficiency groups.

In some embodiments, the botulinum toxin and the positively charged or lipophilic carrier are formulated into a composition before treatment. In some embodiments, the botulinum toxin and the positively charged or lipophilic carrier are formulated into a composition at the point of use.

In some embodiments, the botulinum toxin is at least one selected from a recombinant botulinum toxin, a botulinum toxin derivative, a botulinum toxin complex (including the 150 kD toxin with accessory proteins found in native complexes produced by C. botulinum), a reduced botulinum toxin complex (including the 150 kD toxin with some, but not all, of the native accessory proteins), a purified botulinum toxin of about 150 kDa (the 150 kDa toxin molecule itself, without accessory proteins), or a botulinum toxin fusion protein. In some embodiments, the toxin is a serotype selected from serotype A, B, $C_1$, D, E, F, or G. In preferred embodiments, purified botulinum toxin of about 150 kDa is used, more preferably where in the toxin is of serotype A. In certain embodiments, the carrier is a positively charged carrier or a lipophilic carrier.

Another aspect provides a method of increasing or augmenting bladder contraction intervals associated with a hypercontractility bladder disorder or condition in a subject in need thereof, in which the method comprises administering to a luminal surface of the bladder of the subject an effective amount of a composition comprising a botulinum toxin in conjunction with a positively charged carrier, the carrier comprising a positively charged polymeric backbone having covalently attached thereto one or more positively charged efficiency groups, preferably where the toxin and the carrier associate to form a non-covalent complex. In some embodiments, the botulinum toxin is not covalently linked to the carrier. In some embodiments, the positively charged polymeric backbone of the carrier directly associates non-covalently with the botulinum toxin. In other embodiments, the method comprises administering to a luminal surface of the bladder of the subject an effective amount of a composition comprising a botulinum toxin in conjunction with a lipophilic carrier, the carrier comprising a hydrophobic oligomeric or polymeric backbone with covalently attached thereto one or more positively charged efficiency groups.

In another aspect, the invention provides transmucosal, preferably sterile, compositions comprising a botulinum toxin in conjunction with the positively charged or lipophilic carrier for use in methods of treating or managing a bladder disorder or condition, or in increasing or augmenting bladder contraction intervals associated with a hypercontractility bladder disorder or condition, in a subject in need thereof. Upon contacting a luminal surface of the bladder, compositions described herein can transmucosally deliver botulinum toxin through the urothelium to surrounding structures in an effective amount for treating the subject's bladder disorder or condition. In some embodiments, the composition decreases bladder hypercontractility in the subject, thereby treating the bladder disorder or condition. In preferred embodiments, the bladder disorder or condition is at least one selected from overactive bladder (OAB) or bladder hyperactivity, urge incontinence due to overactive detrusor activity, idiopathic urge incontinence, interstitial cystitis, and bladder pain syndrome. In a particular embodiment, the bladder disorder or condition is overactive bladder (OAB).

According to the present invention, the positively charged or lipophilic carrier is suitable as a transport system for botulinum toxin, enabling the toxin to be transmucosally delivered in the bladder, without covalent modification of the toxin molecule. The positively charged or lipophilic carrier comprises a positively charged or hydrophobic backbone, respectively, to which are covalently attached efficiency groups (also referred to as protein transduction domains (PTDs) or cell-penetrating peptides (CPPs)), more preferably at one or both ends of the backbone. In certain embodiments, the efficiency groups are amino acid sequences selected from the group consisting of HIV-TAT or fragments thereof; the PTD of Antennapedia or a fragment thereof; -(gly)$_{n1}$-(arg)$_{n2}$ (SEQ ID NO: 1) in which the subscript n1 is an integer of from 0 to about 20 and n2 is independently an odd integer from about 5 to about 25; or (gly)$_p$-RGRDDRRQRRR-(gly)$_q$ (SEQ ID NO: 2), (gly)$_p$-YGRKKRRQRRR-(gly)$_q$ (SEQ ID NO: 3), or (gly)$_p$-RKKRRQRRR-(gly)$_q$ (SEQ ID NO: 4), wherein the subscripts p and q are each independently an integer of from 0 to about 20.

In some embodiments, the carrier comprises a polypeptide backbone, preferably polylysine, more preferably a polylysine of about 5 to about 50 residues. In preferred embodiments, the one or more positively charged efficiency groups are attached to either end, or both ends, of the positively charged backbone of the carrier. In some preferred embodiments, the carrier comprises the amino acid sequence YGRKKRRQRRR-G-(K)$_{15}$-G-YGRKKRRQRRR (SEQ ID NO: 9), RGRDDRRQRRR-G-(K)$_{15}$-G-RGRDDRRQRRR (SEQ ID NO: 10), or (G)p-RKKRRQRRR-(G)$_q$-(K)$_n$-(G)$_q$-RKKRRQRRR-(G)$_p$ (SEQ ID NO:8), wherein p is an integer of from 0 to 2, q is an integer of from 0 to 2, and n is an integer of from about 10 to about 20. In a particularly preferred embodiment, the positively charged carrier comprises the amino acid sequence RKKRRQRRRG-(K)15-GRKKRRQRRR (SEQ ID NO: 7).

In particular embodiments, the composition comprises a purified type A botulinum toxin molecule of about 150 kDa in non-covalent association with a positively charged carrier of amino acid sequence RKKRRQRRRG-(K)$_{15}$-GRKKRRQRRR (SEQ ID NO: 7). This composition is referred to herein as "RT003" and is used in the Examples below.

In alternate embodiments, the carrier is a lipophilic carrier comprising palmitoyl-GGRKKRRQRRR (SEQ ID NO: 26), palmitoyl-gly$_p$-KKRPKPG (SEQ ID NO: 27), or oleyl-gly$_p$-KKRPKPG (SEQ ID NO: 29), where p is an integer from 0 to 20.

The compositions described herein can transmucosally deliver botulinum toxin in an effective amount for treating a bladder disorder or condition. In some embodiments, the compositions are administered in an amount of about 1 to about 15 U/kg, about 3 to about 10 U/kg, about 3.3 to about 10 U/kg, about 4 to about 8 U/kg, about 5 to about 7 U/kg, or about 6.5 U/kg; or in an amount of about 0.5 to about 3.5 U/cm$^2$ of bladder surface area, about 0.8 to about 3 U/cm$^2$ of bladder surface area, about 0.84 to about 2.5 U/cm$^2$ of bladder surface area, about 0.9 to about 2.7 U/cm$^2$ of bladder surface area, about 1 to about 2 U/cm$^2$ of bladder surface area, or about 1.5 U/cm$^2$ of bladder surface area; in particular, about 0.84 to about 2.5 U/cm$^2$ of bladder surface area for men and about 0.9 to about 2.7 U/cm$^2$ of bladder surface area for women.

Another aspect of the invention relates to stabilized formulations of the botulinum toxin with the positively charged carrier. In some embodiments, the stabilized formulation further comprises a non-ionic surfactant, such as polysorbate 20 and, optionally, a non-reducing sugar and/or a physiologically compatible buffer for maintaining the pH between 4.5. and 7.5. In preferred embodiments, the toxin in the formulation is stabilized for at least 3 to 4 hours, more preferably over 8 hours, most preferably at least 5 days. A further aspect of the invention relates to dried forms of the stabilized formulations, in particular, a lyophilized form that may be stably stored, distributed, and reconstituted before use.

Yet another aspect of the invention relates to kits providing one or more compositions or formulations described herein for use in a method of the invention. In some embodiments, the kit provides a botulinum toxin and/or a positively charged or lipophilic carrier and/or a device to facilitate topical delivery of the toxin in conjunction with the carrier to the luminal surface of the bladder for transdermal delivery through the luminal mucosal surface. In some embodiments, the toxin is provided as a stabilized formulation. In some embodiments, the toxin is provided in lyophilized form for reconstitution at point of use. In preferred embodiments, the kit further includes a sterile, pharmaceutically acceptable buffer suitable for instillation and for use in reconstitution.

Figure 1:
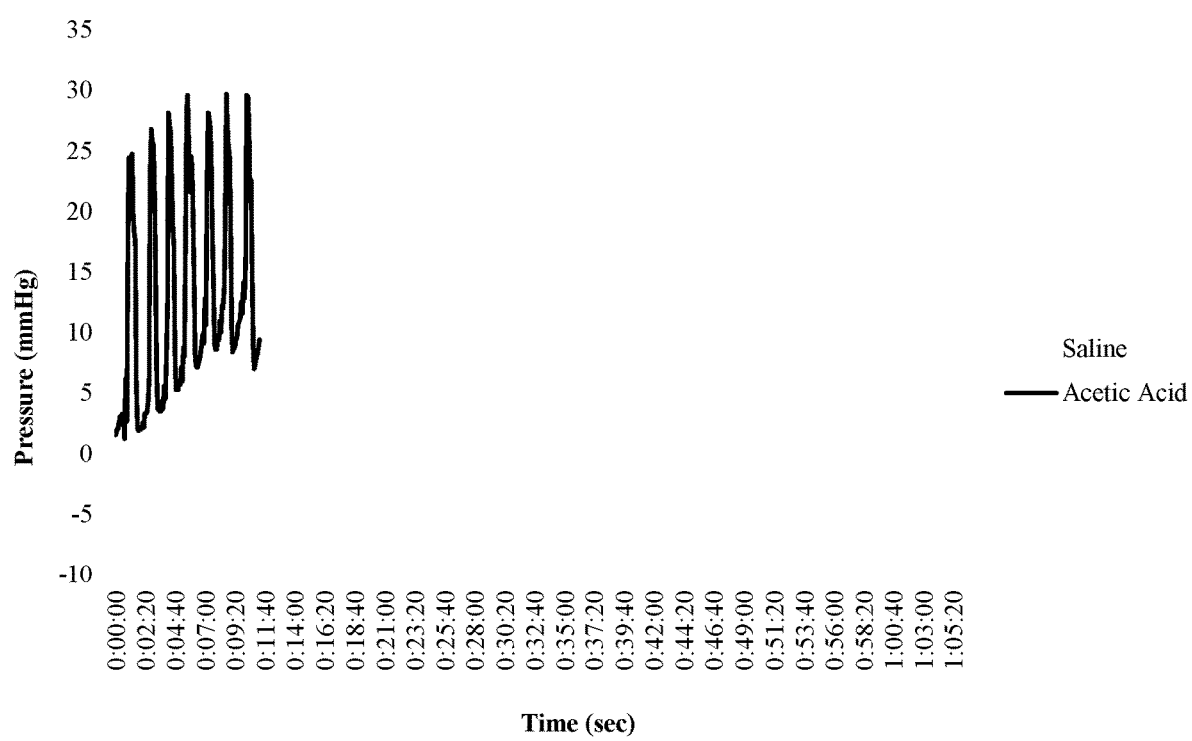
FIG. 1 depicts representative results showing the number of contractions in the bladder of a saline-treated rat (Control); baseline contractions are shown in grey lines and acetic acid-induced hypercontractility is shown in black lines. The interval between contractions is greatly reduced under acetic acid treatment compared to baseline.

Other aspects, features and advantages of the invention will become apparent from the following detailed description and illustrative examples.

DETAILED DESCRIPTION

The present invention provides compositions, kits, and methods for transmucosal delivery of botulinum toxin in the treatment of bladder disorders or conditions using topical administration. Topical administration, with respect to the bladder, refers to introducing botulinum toxin to the inside of the bladder in a manner that allows contact with a luminal surface (mucosal inner lining) of the bladder walls. The invention thus provides compositions and kits for use in administering botulinum toxin to treat bladder disorders or conditions in a patient, without the need to inject the patient with toxin. Current botulinum toxin pharmaceuticals approved for use in the treatment of bladder disorders require multiple injections into the bladder wall, typically delivered via a cystoscope inserted through the urethra. Common problems resulting from cystoscopic injection into the bladder wall include pain, injection puncture through the bladder wall into the peritoneal cavity, bleeding, and incomplete and/or uneven treatment of different areas of the bladder wall, including the significant potential for non-uniform spreading from injection sites. Additional challenges include the need for cystoscopic injection, usually under anesthetic administration, exacerbating the cost of therapy and burden on the patient. The methods of the invention allow for topical administration and transmucosal delivery of botulinum toxin to treat bladder disorders or conditions, providing a significantly less invasive procedure that can be conducted even on an out-patient basis.

Nonlimiting examples of bladder disorders or conditions that may be treated with the compositions, kits, and methods described herein include overactive bladder (OAB) or bladder hyperactivity, urge incontinence due to overactive detrusor activity, idiopathic urge incontinence, interstitial cystitis, and bladder pain syndrome, as well as urinary incontinence, detrusor dysfunction, lower urinary tract dysfunction, urinary retention, urinary hesitancy, polyuria, nocturia, chronic urinary tract infection, a bladder disorder associated with a prostate disorder, bladder neck obstruction, benign prostatic hyperplasia, detrusor external sphincter dyssynergia, detrusor hyperreflexia, detrusor internal sphincter dyssynergia, and a bladder disorder associated with a neurogenic dysfunction (such as, e.g., Parkinson's Disease, multiple sclerosis, spina bifida, transverse myelitis, stroke, spinal cord injury, spasm reflex, and a neurologic lesion of the spinal cord or brain), and other related bladder diseases or dysfunction.

Topical administration and transmucosal delivery, through the luminal surface of the bladder wall, generally is achieved by introduction of botulinum toxin to the lumen of the bladder via the urethra, thereby avoiding the above-noted side effects associated with injection. Injection methods typically are limited to regional injections, using a cytoscope, and thus face access limitations, with restrictions on treating the opposing portion of the bladder wall. Topical administration and transdermal delivery, as described herein, may provide a more even distribution of the toxin throughout the bladder wall, and more complete coverage of the interior of the bladder, thereby resulting in more complete and consistent treatment of the bladder, compared to injection methods. This more even treatment is especially relevant for the reduction of pain experienced in interstitial cystitis, since administration to a greater surface area of the bladder wall than achievable by injections, including all/ most, of the inner bladder wall more effectively treats the bladder disorder or condition, including relieving pain experienced across the entire/most of the bladder, providing superior treatment compared to injection methods.

Transmucosal Delivery for Treatment of Bladder Disorders

In one aspect, the invention provides methods comprising topically administering an effective amount of a botulinum toxin in conjunction with a positively-charged or lipophilic carrier. By "in conjunction with" is meant that the two components (botulinum toxin and carrier) are administered in a combination procedure, which may involve administering to a subject the combination of botulinum toxin and carrier together, or administering them separately, but in a manner such that they act together, such as associating non-covalently to provide for delivery of an effective amount of the toxin.

Topical administration and transmucosal delivery of botulinum toxin, in accordance with the invention, generally is achieved by instillation. As noted above, "instillation," or bladder or intravesical instillation, as used herein, refers to delivery of a liquid or solution to the lumen of the bladder by any means, usually via a catheter introduced into the bladder through the urethra, allowing contact of the liquid or solution, e.g., a solution carrying a botulinum toxin composition, with a portion or all of the luminal surface of the bladder.

Accordingly, in some embodiments, the invention provides methods in which a composition comprising a botulinum toxin in conjunction with a positively charged or lipophilic carrier is administered topically, such as by instillation, to the lumen of the bladder of a subject in need thereof for transmucosal delivery to treat a bladder disorder or condition. It is to be understood that delivery to the bladder encompasses delivery to the mucosal surface of the luminal bladder wall, which is referred to herein as the luminal surface of the bladder. The innermost surface of the bladder is a mucosal layer, lining the hollow lumen, which provides a unique mucosal surface. For example, unlike mucosa of other hollow organs, the mucosa of the inner walls of the bladder is composed of "transitional epithelium" or "urothelium," which is able to stretch to accommodate changes in the volume of urine. A deeper level is the "lamina propria," followed by a "submucosa" layer, which itself is surrounded by smooth muscle. The submucosa is a layer of connective tissue with blood vessels and nerves that supports and controls the surrounding tissue layers. The smooth muscle layer (muscularis) surrounding the submucosa provides the bladder with its ability to expand and contract. The smooth muscle making up most of the bladder walls is called the detrusor muscle. Contraction of this muscle is mainly responsible for emptying the bladder during voiding. The muscularis also forms the internal urethral sphincter, a ring of muscle that surrounds the urethral opening and holds urine in the urinary bladder. Instillation of a solution comprising botulinum toxin, as disclosed herein, permits contact with a portion, preferably a significant portion, more preferably most or all, of the inner mucosal surface (luminal surface) of the bladder wall and facilitates transmucosal delivery of the toxin through the urothelium to surrounding muscles and nerve structures.

Generally, a botulinum toxin formulation for topical administration is introduced to the lumen of the bladder using an "instillation device," that typically comprises a catheter. The catheter may be inserted into the lumen of the bladder through the urethra ("transurethral delivery"), and the formulation infused through, so that it contacts the luminal surface of the bladder, e.g., coating at least a portion, more preferably most, and still more preferably nearly all or all, of the inner lining of the bladder wall. The instillation device used for topical administration of compositions described herein may be simple in construction or may be a more complicated device that includes means for dispensing and monitoring the dispensing of the composition, and optionally means for monitoring the condition of the subject (e.g., monitoring the reaction of the subject to the composition being administered).

Nonlimiting examples of instillation devices for carrying out methods described herein include standard urethral catheters such as, for example, BARDEX® I.C., 2-way catheter, part #0165SI14 Balloon 5 cc, 14FR latex; Foley Catheters, LUBRI-SIL®, 2-way, part #175814 Balloon 5 cc, 14FR silicone; Coloplast 14 fr catheter: SELF-CATH® part number: 450, 14 FR Uncoated, HCPCS code: A4351, 16 inch PVC Straight Tip 50. Other transurethral catheters that may be used for bladder instillation of compositions described herein can be found, e.g., in WO 2011/053554 (PCT/US2010/053959), Ruegg et al. "Device and Method for Topical Application of Therapeutic or Cosmetic Compositions," as well as devices typically used for bladder wash, such as low-pressure profusion devices, Fr14 gauge catheters, balloon catheters, sprays, and the like. Similar devices may be used for rinsing residual botulinum toxin from the bladder following treatment, e.g., with sterile saline.

It will be appreciated that the choice of materials for the construction of the device is important. Preferred materials for the construction of instillation devices are those that do not lead to loss of activity of the botulinum toxin/carrier solution, either through degradation or unwanted adsorption of the botulinum toxin on a surface of the device. Such undesired behavior has been observed, for example, when botulinum toxin/carrier in an aqueous solution contacts polypropylene surfaces, but not when the botulinum toxin/carrier solution contacts polyvinyl chloride (PVC) surfaces.

In some embodiments, a balloon catheter is used as the instillation device, where the balloon end of the catheter is comprised of an inner bag that is inflated with air or an inert gas once in place and an outer concentric bag/sheath that has spaced holes (preferably regularly-spaced holes) to allow for delivery of a liquid or solution, such as a solution comprising a botulinum toxin composition for topical administration and transmucosal delivery. Once the catheter is inserted transurethrally and the balloon is positioned in the bladder, air is injected into the inner compartment to inflate the balloon to a point where it occupies the lumen of the bladder. The solution may then be instilled through the catheter, such that it is released through the holes in the outer bag and into the lumen of the bladder. The inflated inner bag helps to maximize coverage of the luminal surface of the bladder with the available volume of solution, thereby maximizing direct topical contact of the toxin with the target tissue (mucosal lining of the bladder walls).

In some embodiments, the volume of solution used is from about 10 to 400 mL, 20 to 200 mL, 30 to 100 mL, or 40 to 60 mL, preferably about 50 mL. The solution is allowed to remain in the lumen of the bladder for a suitable amount of time to allow for topical application and transmucosal delivery of toxin, e.g., about 1 minute to 4 hours, 15 minutes to 2 hours, 30 to 90 minutes, preferably about 60 minutes, more preferably about 15 minutes to about 30 minutes, such as, in a particular example, about 30 minutes. After this time, the balloon may be deflated and the catheter removed. In a particular embodiment, an aqueous formulation comprising a botulinum toxin, such as botulinum toxin of subtype A, and a positively charged or lipophilic carrier, as described herein, is instilled into the bladder of a subject via a catheter, and the catheter is clamped for about 15 to 30 minutes. Optimally, during this period of time, the subject physically changes position every few minutes to help coat the entire inner lining of the bladder with the instilled aqueous formulation. At the end of the treatment period, the aqueous formulation can be drained from the subject's bladder, e.g., by voiding, and the catheter removed. Voided formulations preferably are collected and/or inactivated prior to disposal, e.g., as described below, to prevent accidental contact with botulinum toxin.

The composition comprising botulinum toxin and the positively charged or lipophilic carrier may be prepared, e.g., reconstituted, prior to instillation of the composition to the bladder, or the composition may be formed in situ following instillation of each of the components (carrier and toxin) separately into the bladder.

In some embodiments, the method of the invention further involves monitoring the effect of the composition administered on bladder function. In a particular embodiment, cystometry, also known as flow cystometry, is used to evaluate bladder function by measuring contractile force of the bladder when voiding. A voiding chart generated from cystometric analysis is known as a cystometrogram (CMG), which plots volume of liquid emptied from bladder against intravesical (or intraluminal) pressure. Cystometric analysis is used to evaluate the bladder's capacity to contract and expel urine.

The cystometry procedure generally will be conducted as known in the art. The procedure usually is short, ranging from fifteen minutes to an hour. It may involve the insertion of one or two catheters into an emptied bladder through the urethra. In the two catheter method, one catheter transfers liquid while the other is a manometer (pressure sensor). In the single catheter method, a specialized catheter performs both the transfer and pressure sensing functions. An additional rectal catheter may also be placed for additional data. Typically, the bladder is filled with saline and, if the procedure is applied to a human subject, the practitioner queries the subject's awareness of the event. Accordingly, the subject is often asked to note when presence of liquid is felt, when the bladder feels full, and when the urgency to void is felt. The subject is then asked to void, and both flow and pressure are recorded. Flow and pressure are plotted against each other to create the cystometrogram, in which the x-axis is the volume of liquid and the y-axis is the intraluminal pressure of the bladder. In normal subjects, the plot is a series of spikes whose local minimums form a non-linear curve resembling an exponential growth curve. Monitoring the effect of the transmucosal composition on bladder function facilitates administration of an effective amount, as described below.

Following bladder instillation of botulinum toxin, as disclosed herein, the toxin may be removed and/or inactivated. Generally, after removal of the catheter used for bladder instillation, the patient is encouraged to void his/her bladder to expel residual unabsorbed amounts of the toxin, e.g., into a toilet or bedpan. The bladder may be further rinsed one or more times to "wash out" or remove residual amounts, e.g., using a different catheter for instillation of a rinsing solution, such as sterile saline. The toxin composition may further be removed and/or inactivated, e.g., using any of the removal and/or inactivation approaches described in WO2012094163 A1 (PCT/US2011/066728), Waugh et al., "Methods and Kits for Topical Application, Removal, and Inactivation of Therapeutic or Cosmetic Toxin Compositions," incorporated herein by reference in its entirety. For example, following treatment, the patient may void his/her bladder into a toilet or bedpan that contains a dilute solution of bleach in order to inactivate residual toxin. Voided toxin may be treated as biohazard waste, e.g., transferred to a biohazard container, preferably employing precautions typically used when handling bio hazardous materials (use of disposable gloves, warning labels, etc.).

Transmucosal Compositions

Transmucosal compositions of this invention, in preferred embodiments, stabilize the botulinum toxin and/or enable its delivery through the urothelium of the bladder wall, allowing the toxin molecule to penetrate tissue layers impermeable to botulinum toxin formulations lacking carriers described herein. The transmucosal compositions comprise a botulinum toxin in non-covalent association with an effective amount of the carrier, which can be a lipophilic carrier or a positively charged carrier that comprises positively charged "efficiency groups," also referred to as protein transduction domains (PTDs) or cell-penetrating peptides (CPPs). Lipophilic carriers comprise a hydrophobic backbone to which is covalently attached the positively charged efficiency groups; positively charged carriers comprise a positively charged backbone, to which is covalently attached the positively charged efficiency groups.

According to the present invention, the positively charged or lipophilic carrier is suitable as a transport system for botulinum toxin, enabling the toxin to be delivered without covalent modification of the toxin molecule across mucosal membranes.

The following sections describe the various components of the compositions for use in the present invention.

The Botulinum Toxin Component

The term "botulinum toxin" as used herein may refer to any of the known types of botulinum toxin (e.g., 150 kD botulinum toxin protein molecules associated with the different serotypes of C. botulinum), whether produced by the bacterium or by recombinant techniques, as well as any types that may be subsequently discovered including newly discovered serotypes, and engineered variants or fusion proteins. As mentioned above, currently seven immunologically distinct botulinum neurotoxins have been characterized, namely botulinum neurotoxin serotypes A, B, C1, D, E, F and G, each of which is distinguished by neutralization with type-specific antibodies. The different serotypes of botulinum toxin vary in the animal species that they affect and in the severity and duration of the paralysis they evoke. In preferred embodiments, the composition comprises a botulinum toxin of serotype A.

The botulinum toxin serotypes are commercially available, for example, from Sigma-Aldrich (St. Louis, MO) and from Metabiologics, Inc. (Madison, WI), as well as from other sources. At least two types of botulinum toxin, types A and B, are available commercially in formulations for treatment of certain conditions. Type A, for example, is contained in preparations of Allergan, Inc., having the trademark BOTOX®, as well as in preparations of Ipsen Limited, having the trademark DYSPORT®. The original Botox® formulation, was prepared by Schantz in 1979 (Schantz et al., "Preparation and characterization of botulinum toxin type A for human treatment" *Therapy with Botulinum Toxin*. Vol. 109. New York, NY: Marcel Dekker; 1994. pp. 10-24). Type B is contained, for example, in preparations of Elan Pharmaceuticals having the trademark MYOBLOC®. Recombinant botulinum toxin can also be purchased, e.g., from List Biological Laboratories, Campbell, CA.

The term "botulinum toxin" can alternatively refer to a botulinum toxin derivative, that is, a compound that has botulinum toxin activity but contains one or more chemical or functional alterations on any part or on any amino acid chain relative to naturally occurring or recombinant native botulinum toxins. For instance, the botulinum toxin may be a modified neurotoxin that is a neurotoxin which has at least one of its amino acids deleted, modified, or replaced, as compared to a native form, or the modified neurotoxin can be a recombinantly produced neurotoxin or a derivative or fragment thereof. For instance, the botulinum toxin may be one that has been modified in a way that, for instance, enhances its properties or decreases undesirable side effects, but that still retains the desired botulinum toxin activity. Alternatively the botulinum toxin used in this invention may be a toxin prepared using recombinant or synthetic chemical techniques, e.g., a recombinant peptide, a fusion protein, or a hybrid neurotoxin, for example prepared from subunits or domains of different botulinum toxin serotypes (See, U.S. Pat. No. 6,444,209, for instance). The botulinum toxin may also be a portion of the overall molecule that has been shown to possess the necessary botulinum toxin activity and, in such case, may be used per se or as part of a combination or conjugate molecule, for instance a fusion protein. Alternatively, the botulinum toxin may be in the form of a botulinum toxin precursor, which may itself be non-toxic, for instance a non-toxic zinc protease that becomes toxic on proteolytic cleavage.

The term "botulinum toxin complex," or "toxin complex," as used herein refers to the approximately 150 kD botulinum toxin protein molecule (belonging to any one of botulinum toxin serotypes A-G), along with associated endogenous non-toxin proteins (i.e., hemagglutinin protein and non-toxin non-hemagglutinin protein produced by C. botulinum bacteria). In some embodiments, the botulinum toxin complex need not be derived from C. botulinum bacteria as one unitary toxin complex, but rather may be, for example, botulinum toxin that is recombinantly prepared first and then subsequently combined with the non-toxin proteins.

The term "reduced botulinum toxin complex," or "reduced toxin complex," refers to botulinum toxin complexes having reduced amounts of non-toxin protein compared to the amounts naturally found in botulinum toxin complexes produced by C. botulinum bacteria. Reduced botulinum toxin complexes may be prepared using any conventional protein separation method to extract a fraction of the hemagglutinin protein or non-toxin non-hemagglutinin protein from botulinum toxin complexes derived from the bacteria. For example, reduced botulinum toxin complexes may be produced by dissociating botulinum toxin complexes through exposure to red blood cells at a pH of 7.3, HPLC, dialysis, columns, centrifugation, and other methods for extracting proteins from complexes. Other procedures that can be used are described in, e.g., U.S. Pat. No. 9,469,849 to Ruegg, entitled "Methods And Systems For Purifying Non-Complexed Botulinum Neurotoxin;" WO 2006/096163 to Allergan, Inc., entitled "Animal Product Free System And Process For Purifying A Botulinum Toxin;" EP 1514556 B1, to Allergan, Inc., entitled "Botulinum toxin pharmaceutical compositions," and WO 2010/078242 A1 (PCT/US2009/069576), Ruegg et al., "Injectable Botulinum Toxin Formulation," each hereby incorporated herein by reference in its entirety. Alternatively, when the reduced botulinum toxin complexes are to be produced by combining synthetically produced botulinum toxin with non-toxin proteins, a reduced botulinum toxin complex is obtained by using less hemagglutinin or non-toxin, non-hemagglutinin protein in the mixture than what would be present in naturally occurring botulinum toxin complexes.

Any of the non-toxin proteins (e.g., hemagglutinin protein or non-toxin non-hemagglutinin protein or both) in the reduced botulinum toxin complexes may be reduced independently, by any amount. For example, although the amount of endogenous non-toxin proteins may be reduced by the same amount in some cases, this invention also contemplates reducing each of the endogenous non-toxin proteins by different amounts, as well as reducing at least one of the endogenous non-toxin proteins, but not the others.

In certain exemplary embodiments, one or more non-toxin proteins are reduced by at least about 0.5%, 1%, 3%, 5%, 10%, 20%, 30%, 40%, 50%, 60%, 70%, 80%, 90% or 100% compared to the amounts normally found in botulinum toxin complexes. As noted above, C. botulinum bacteria produce seven different serotypes of toxin. Commercial preparations are manufactured with different relative amounts of non-toxin proteins. For example, MYOBLOC® has 5000 U of Botulinum toxin type B per ml with 0.05% human serum albumin, 0.01 M sodium succinate, and 0.1 M sodium chloride. DYSPORT® has 500 U of botulinum toxin type A-hemagglutinin complex with 125 mcg albumin and 2.4 mg lactose. In certain embodiments, substantially all of the non-toxin protein (e.g., greater than 95%, 96%, 97%, 98% or 99% of the hemagglutinin protein and non-toxin non-hemagglutinin protein) that would normally be found in botulinum toxin complexes derived from C. botulinum bacteria is removed from the botulinum toxin complex.

Accordingly, in various embodiments, the botulinum toxin component of the present compositions can be selected from a botulinum toxin complex (including the 150 kD neurotoxin with accessory proteins found in native complexes produced by C. botulinum bacteria, as described above), a reduced botulinum toxin complex (including the 150 kD neurotoxin with some, but not all, of the native accessory proteins), and the 150 kD botulinum toxin molecule itself, without accessory proteins. In preferred embodiments, the botulinum toxin is a purified molecule of about 150 kDa. Methods of purifying the 150 kDa toxin are known in the art, see, for example, WO 2011/050072 A1 (PCT/US2010/053389), Ruegg "Methods and Systems for Purifying Non-Complexed Botulinum Neurotoxin," incorporated herein in its entirety.

Botulinum toxin activity can be assessed using procedures known in the art, e.g., measuring units (U) of botulinum toxin activity. Median lethality assays ($LD_{50}$ assays) in mice are conventionally used to estimate the number of units of botulinum toxin with a high degree of precision. The amount and/or activity of the botulinum toxin in prepared formulations and compositions can be assessed using procedures practiced in the art. For example, the AlphaLISA assay, which uses two monoclonal antibodies, each specific for a distinct epitope of botulinum toxin A, may be used to quantify botulinum toxin A concentration in the ng/mL range. Alternatively or in addition, a potency test using mouse $LD_{50}$ may be conducted to confirm that the expected biological activity of the botulinum toxin is present. Alternatively, an HPLC assay can be used to confirm that the appropriate amount of positively charged carrier peptide is maintained in the formulation.

By way of example, one unit of botulinum toxin corresponds to the calculated median intraperitoneal lethal dose (LD50) in female Swiss-Webster mice. See, Hoffman, R. O. et al., 1986, Int. Ophthalmol. Clin., 26:241-50, as well as DePass, L. R., 1989, Toxicol. Letters, 49:159-170; and Pearce, L. B. et al., 1994, Toxicol. Appl. Pharmacol., 128: 69-77, which also describe lethality assays in the art. More particularly, a suitable method for determining botulinum toxin units is as follows: Forty-eight (48) female CD-1 mice weighing 17-23 grams are randomly assigned to six doses of the test article (1.54, 1.31, 1.11, 0.95, 0.80, and 0.68 U/0.5 mL), eight (8) animals per dose group. The test article refers to the botulinum toxin preparation or sample being assayed or tested. The animals are housed eight per cage and are weighed within 24 hours of dosing with the test article. On the day of dosing, the test article is diluted to the appropriate concentrations in isotonic saline (0.9% NaCl). Each animal is administered 0.5 mL of diluted test article via intraperitoneal injection. After injection, mice are returned to the cage and fatalities are recorded daily for three days. Lethality is scored 72 hours post-injection and the results are analyzed by probit or logistic analysis to derive the $LD_{50}$ value relative to a reference standard that is assessed using the same dosing regimen.

In the present composition, botulinum toxin generally non-covalently associates with a carrier to form a complex without covalent modification to the botulinum toxin molecule. The association between the carrier and the botulinum toxin involves one or more types of non-covalent interaction, non-limiting examples of which include ionic interactions, hydrogen bonding, van der Waals forces, or combinations thereof. For example, in preferred embodiments, the positively charged or lipophilic backbone and the botulinum toxin directly contact to form a non-covalent complex, associating by non-covalent interactions. See also, e.g., WO 2005/084410 (PCT/US2005/007524), to Dake et al., "Compositions and Methods for Topical Application and Transdermal Delivery of Botulinum Toxins," further describing how non-covalent association avoids the need to covalently modify the toxin molecule being delivered. The carrier molecules for use in the compositions are described below.

Carrier Molecules

According to the present invention, a positively charged or lipophilic carrier molecule, having covalently attached efficiency groups, as described herein, may serve as a transport system for botulinum toxin in the treatment and management of bladder disorders or conditions. In certain embodiments, the positively charged or lipophilic carrier will not have other enzymatic or therapeutic biologic activity.

In the transdermal compositions, a positively charged or lipophilic carrier has the effect of promoting translocation of botulinum toxin through a tissue or cell membrane, such a through the urothelium of the bladder wall, overlying muscles and nerve structures associated with the bladder disorder or condition to be treated. The translocation occurs, in preferred embodiments, without covalent modification of the botulinum toxin.

In certain embodiments, the positively charged or lipophilic carrier is the sole agent necessary for transdermal delivery of the botulinum toxin across the urothelium of the bladder wall. In preferred embodiments, the concentration of positively charged or lipophilic carriers in the compositions is sufficient to enhance delivery of the botulinum toxin to surrounding muscles and nerve structures. Furthermore, without wishing to be bound by theory, it is believed that the penetration rate follows receptor-mediated kinetics, such that tissue penetration increases with increasing amounts of positively charged or lipophilic carrier up to a saturation point, upon which the transport rate becomes constant. Thus, in a preferred embodiment, the amount of carrier corresponds to the amount that maximizes penetration rate right before saturation. A useful concentration range for the positively charged or lipophilic carrier in the transmucosal compositions of the invention is about 1.0 pg/U to 0.5 mg/U of botulinum toxin (amount of carrier/U of botulinum toxin), preferably in a range of about 100 pg to about 1 mcg/U, more preferably in a range of about 50 ng/U to about 150 ng/U, and most preferably about 90 ng/U to about 110 ng/U, and in a particular example, about 100 ng/U or about 94 ng/U. Preferably, the botulinum toxin is of serotype A, and particularly, the 150 kD form of serotype A botulinum toxin.

Preferably, the positively charged or lipophilic carrier includes positively charged efficiency groups in an amount of at least about 0.01%, as a percentage of the total carrier weight, preferably from about 0.01 to about 75 weight percent, more preferably from about 0.05 to about 60 weight percent, more preferably from about 0.1 to about 30, and most preferably from about 55 to about 65, weight percent. In one embodiment, the efficiency groups are about 59% by weight of the total weight of the positively charged or lipophilic carrier. For positively charged protein transduction domains having the formula -(gly)$_{n1}$-(arg)$_{n2}$, a preferred range is from about 0.1 to about 25%, more preferably about 40 to about 70%.

Exemplary positively charged carriers that can be used in transdermal compositions of the invention are described, e.g., in WO 2002/007773 (PCT/US2001/023072) to Waugh et al., "Multi-Component Biological Transport Systems;" WO 2005/084410 (PCT/US2005/007524), to Dake et al., "Compositions and Methods for Topical Application and Transdermal Delivery of Botulinum Toxins;" WO 2010/151840 (PCT/US2010/040104) to Thompson et al., "Albumin-Free Botulinum Toxin Formulations"; WO 2009/015385 (PCT/US2008/071350) to Stone et al., "Antimicrobial Peptide, Compositions, and Methods of Use;" WO 2013/112974 (PCT/US2013/023343) to Waugh et al., "Methods and Assessment Scales for Measuring Wrinkle Severity;" and/or WO 2014/066916 (PCT/US2013/67154) to Ruegg et al. "Compositions and Methods for Safe Treatment of Rhinitis;" exemplary lipophilic carriers that may be used in topical compositions of the present invention are described, e.g., in US 2016/0166703 A1 to Tan et al., entitled "Carrier Molecule Compositions and Related Methods" and in US 2014/0056811 A1 to Jacob, et al., entitled "New Cell-Penetrating Peptides And Uses Thereof," each of which is incorporated herein by reference in its entirety.

In an alternative embodiment, the carrier molecule may comprise multiple domains that may include domains such that at least one domain is a group that enhances transmucosal transport and which typically comprises a plurality of positively charged amino acids. Other domains may also contribute to facilitating transmucosal transport, non-covalent association with botulinum toxin, or serve as linker groups with or without contributing to charge.

By the use of the terms "positively charged" or "cationic," it is meant that the carrier has a positive charge under at least some solution-phase conditions, more preferably, under at least some physiologically compatible conditions. More specifically, "positively charged" or "cationic" means that the group in question contains functionalities that are charged under physiological pH conditions, for instance, a quaternary amine, or that the group contains a functionality which can acquire positive charge under certain solution-phase conditions, such as pH changes in the case of primary amines. More preferably, "positively charged" or "cationic" as used herein refers to those groups that have the behavior of associating with anions over physiologically compatible conditions. Generally, the positively charged carrier comprises a positively charged backbone, described in more detail below.

Positively Charged Backbones of the Carrier Molecules

The positively charged backbone typically is a chain of atoms, either with groups in the chain carrying a positive charge at physiological pH, or with groups carrying a positive charge attached to side-chains. Generally, the backbone is a linear hydrocarbon backbone which is, in some embodiments, interrupted by heteroatoms selected from nitrogen, oxygen, sulfur, silicon, and phosphorus. The majority of backbone chain atoms are usually carbon. Additionally, the backbone will often be a polymer of repeating units (e.g., amino acids, poly(ethyleneoxy), poly(propyleneamine), polyalkyleneimine, and the like) and can be a homopolymer or a heteropolymer.

In certain preferred embodiments, the positively charged backbone comprises a cationic peptide, such as a polypeptide having multiple positively charged sidechain groups (e.g., lysine, arginine, ornithine, homoarginine, and the like). As used herein, the term "peptide" refers to an amino acid sequence, but carries no connotation with respect to the number of amino acid residues within the amino acid sequence. Accordingly, the term "peptide" may also encompass polypeptides and proteins. For example, cationic peptide backbones of the invention may comprise from about 5 to about 100 amino acid residues, from about 10 to about 50 amino acid residues, or from about 12 to about 20 amino acid residues. In preferred embodiments, the cationic peptide backbone comprises 10 to 20 amino acids, or 10, 11, 12, 13, 14, 15, 16, 17, 18, 19, or 20 amino acids, preferably being polylysine amino acid residues. One of skill in the art will appreciate that when amino acids are used in this portion of the invention, the sidechains can have either the D- or L-form (R or S configuration) at the center of attachment.

In particularly preferred embodiments, the positively charged backbone is a polylysine. In some embodiments, the polylysine may have a molecular weight that is at least about 100, 200, 300, 400, 500, 600, 700, 800, 900, 1000, 1500, 2000, 2500, 3000, 3500, 4000, 4500, 5000, 5500, or 6000 D, and less than about 2,000,000, 1,000,000, 500,000, 250,000, 100,000, 75,000, 50,000, and 25,000 D. Within the range of 100 to 2,000,000 D, it is contemplated that the lower and/or upper range may be increased or decreased, respectively, by 100, with each resulting sub-range being a specifically contemplated embodiment of the invention. The polylysine contemplated by this invention can be any of the commercially available (Sigma Chemical Company, St. Louis, Mo., USA) polylysines such as, for example, polylysine having MW>70,000, polylysine having MW of 70,000 to 150,000, polylysine having MW 150,000 to 300,000 and polylysine having MW>300,000.

In some preferred embodiments, the polylysine has a molecular weight from about 1,000 to about 1,500,000 D, from about 2,000 to about 800,000 D, or from about 3,000 to about 200,000 D. In more preferred embodiments, the polylysine has molecular weight from about 100 to about 10,000 D, from about 500 to about 5,000 D, from about 1,000 to about 4,000 D, from about 1,500 to about 3,500 D, or from about 2,000 to about 3,000 D. Especially preferred is a polylysine polypeptide having 10 to 20 lysines, more preferably, 15 lysines (SEQ ID NO: 33). The selection of an appropriate polylysine will depend on the remaining components of the composition and will be sufficient to provide an overall net positive charge to a positively charged carrier.

In another embodiment, the positively charged backbone is a nonpeptidyl polymer, which may be a hetero- or homo-polymer such as a polyalkyleneimine, for example a polyethyleneimine or polypropyleneimine. In some embodiments, the positively charged backbone is a polypropyleneamine wherein a number of the amine nitrogen atoms are present as ammonium groups (tetra-substituted) carrying a positive charge. In another group of embodiments, the backbone has attached a plurality of side-chain moieties that include positively charged groups (e.g., ammonium groups, pyridinium groups, phosphonium groups, sulfonium groups, guanidinium groups, or amidinium groups).

Alternatively, the backbone may comprise amino acid analogs and/or synthetic amino acids. The backbone may also be an analog of a polypeptide such as a peptoid. See, for example, Kessler, Angew. Chem. Int. Ed. Engl. 32:543 (1993); Zuckermann et al. Chemtracts-Macromol. Chem. 4:80 (1992); and Simon et al. Proc. Nat'l. Acad. Sci. USA 89:9367 (1992)). Briefly, a peptoid is a polyglycine in which the sidechain is attached to the backbone nitrogen atoms rather than the α-carbon atoms. As above, a portion or all of the sidechains will typically terminate in a positively charged group to provide a positively charged backbone component. Synthesis of peptoids is described in, for example, U.S. Pat. No. 5,877,278, which is hereby incorporated by reference in its entirety. As the term is used herein, positively charged backbones that have a peptoid backbone construction are considered "non-peptide" as they are not composed of amino acids having naturally occurring sidechains at the alpha-carbon locations.

A variety of other backbones can be used employing, for example, steric or electronic mimics of polypeptides wherein the amide linkages of the peptide are replaced with surrogates, such as ester linkages, thioamides (—CSNH—), reversed thioamide (—NHCS—), aminomethylene (—NHCH$_2$—) or the reversed methyleneamino (—CH$_2$NH—) groups, keto-methylene (—COCH$_2$—) groups, phosphinate (—PO$_2$RCH$_2$—), phosphonamidate and phosphonamidate ester (—PO$_2$RNH—), reverse peptide (—NHCO—), trans-alkene (—CR=CH—), fluoroalkene (—CF=CH—), dimethylene (—CH$_2$CH$_2$—), thioether (—CH$_2$S—), hydroxyethylene (—CH(OH)CH$_2$—), methyleneoxy (—CH$_2$O—), tetrazole (CN$_4$), sulfonamido (—SO$_2$NH—), methylenesulfonamido (—CHRSO$_2$NH—), reversed sulfonamide (—NHSO$_2$—), and backbones with malonate and/or gem-diamino-alkyl subunits, for example, as reviewed by Fletcher et al. ((1998) Chem. Rev. 98:763) and detailed by references cited therein. Many of the foregoing substitutions result in approximately isosteric polymer backbones relative to backbones formed from alpha-amino acids.

When the carrier comprises a relatively short linear polylysine or PEI backbone, the backbone will have a molecular weight of less than 75,000 D, more preferably less than 30,000 D, and most preferably, less than 25,000 D. When the carrier is a relatively short branched polylysine or PEI backbone, however, the backbone will have a molecular weight less than 60,000 D, more preferably less than 55,000 D, and most preferably less than 50,000 D.

In one particularly preferred embodiment, the carrier comprises a relatively short polylysine or polyethyleneimine (PEI) backbone (which may be linear or branched) and which has positively charged efficiency groups covalently attached. In more particularly preferred embodiments, the positively charged backbone is a polylysine and positively charged efficiency groups are attached to the lysine at the C- and/or N termini. The efficiency groups are described in detail below.

Efficiency Groups

Generally, the positively charged or hydrophobic backbone, has covalently attached one or more efficiency groups (PTDs or CPPs). The efficiency groups can be placed at spacings along the backbone that are consistent in separations or variable. In preferred embodiments, the one or more efficiency groups are attached to either end, or more preferably to each of the two ends, of the backbone of the carrier. Additionally, the length of the efficiency groups can be similar or dissimilar. In embodiments using peptoid backbones, as provided above, efficiency groups can be covalently attached at various atoms or groups of the backbone. For example, the sulfonamide-linked backbones (—SO$_2$NH— and —NHSO$_2$—) can have efficiency groups attached to the nitrogen atoms. Similarly, the hydroxyethylene (—CH(OH)CH$_2$—) linkage can bear efficiency groups attached to the hydroxy substituents. One of skill in the art can readily adapt the other linkage chemistries to provide efficiency groups using standard synthetic methods.

As used herein, an "efficiency group" is any agent that has the effect of promoting the translocation of the positively charged or hydrophobic backbone through a tissue or cell membrane and/or improving delivery of a molecule associated with the backbone to a target site. Non-limiting examples of efficiency groups include HIV-TAT or fragments thereof, the PTD of Antennapedia or a fragment thereof, or -(gly)$_{n1}$-(arg)$_{n2}$ (SEQ ID NO: 1) in which the subscript n1 is an integer of from 0 to about 20, more preferably 0 to about 8, still more preferably about 2 to about 5, and the subscript n2 is independently an odd integer of from about 5 to about 25, more preferably about 7 to about 17, most preferably about 7 to about 13.

In some embodiments, the HIV-TAT fragment does not contain the cysteine-rich region of the HIV-TAT molecule, in order to minimize the problems associated with disulfide aggregation. Preferably, the fragments of the HIV-TAT and Antennapedia PTDs retain the protein transduction activity of the full protein. A preferred efficiency group is, for example, -Gly$_3$Arg$_7$ (SEQ ID NO: 5). Still further preferred efficiency groups, in some embodiments, are those where the HIV-TAT fragment has the amino acid sequence (gly)$_p$-RGRDDRRQRRR-(gly)$_q$ (SEQ ID NO: 2), (gly)$_p$-YGRKKRRQRRR-(gly)$_q$ (SEQ ID NO: 3), or (gly)$_p$-RKKRRQRRR-(gly)$_q$ (SEQ ID NO; 4), wherein the subscripts p and q are each independently an integer of from 0 to about 20, or wherein p and q are each independently the integer 1. In certain preferred embodiments, p is one and q is zero or p is zero and q is one. Preferred HIV-TAT fragments are those in which the subscripts p and q are each independently integers of from 0 to 8, more preferably 0 to 5. In some embodiments, the fragment or efficiency group is attached to the backbone via either the C-terminus or the N-terminus of the fragment or amino acid sequence of the efficiency group. In preferred embodiments, the one or more positively charged efficiency groups are attached to either end, or both ends, of the positively charged backbone of the carrier.

In some embodiments, the efficiency groups are the Antennapedia (Antp) PTD, or a fragment thereof that retains activity. These are known in the art, for instance, from Console et al., *J. Biol. Chem.* 278:35109 (2003) and a non-limiting example of an Antennapedia PTD contemplated by this invention is the PTD having the amino acid sequence SGRQIKIWFQNRRMKWKKC (SEQ ID NO: 6).

In some particularly preferred embodiments, the positively charged carrier is a positively charged peptide having the amino acid sequence RKKRRQRRR-G-(K)$_{15}$-G-RKKRRQRRR (SEQ ID NO: 7); or a positively charged peptide having the amino acid sequence (G)$_p$-RKKRRQRRR-(G)$_q$-(K)$_n$-(G)$_q$-RKKRRQRRR-(G)$_p$ (SEQ ID NO:8), YGRKKRRQRRR-G-(K)$_{15}$-G-YGRKKRRQRRR (SEQ ID NO: 9); or a positively charged peptide having the amino acid sequence RGRDDRRQRRR-G-(K)$_{15}$-G-RGRDDRRQRRR (SEQ ID NO: 10) for use in the compositions and methods of the invention.

In some embodiments, the efficiency groups comprise a peptide having the amino acid KLAKLAK (SEQ ID NO: 11). Other exemplary efficiency groups include any of the CPPs disclosed in US 2014/0056811 A1 to Jacob, et al., entitled "New Cell-Penetrating Peptides And Uses Thereof," incorporated herein by reference in its entirety.

Backbones and Efficiency Groups for Lipophilic Carriers

Lipophilic carriers generally comprise a hydrophobic oligomeric or polymeric backbone, to which one or more efficiency groups are covalently attached. In particular examples where the carrier is lipophilic, the efficiency group may be selected from any of the efficiency groups described above, for example, an HIV-TAT fragment, as described herein. In addition, the efficiency group may be selected from one or more of the following: KKRPKPG (SEQ ID NO: 12); AAVLLPVLLAAP (SEQ ID NO: 13) (prion); RRRRRRRRR (SEQ ID NO: 14); RQIKWFQNRRMKWKK (SEQ ID NO: 15) (Antennapedia fragment); NPGGYCLTKWMILAAELKCFGNTA-VAKCNVNHDAEFCD (SEQ ID NO: 16) (Transduction Domain 1); GIGAVLKVLTTGLPALISWIKRKRQQ (SEQ ID NO: 17) (melittin); (gly)$_p$-KKRPKPG-(gly)$_q$ (SEQ ID NO: 18), wherein the subscripts p and q are each independently an integer from 0 to about 20; FLVFFFGG (SEQ ID NO: 19); and gly$_{n1a}$-KKRPQPD-gly$_{n1b}$ (SEQ ID NO: 20), where the subscripts n1a and n1b are each integers of from 0 to about 20.

In addition, where the carrier is a lipophilic carrier, a wide variety of synthetic or otherwise man-made efficiency groups may be used in various embodiments, including for example, KKRPKPGGGGFFFILVF (SEQ ID NO: 21), FFFILVFGGGKKRPKPG (SEQ ID NO: 22), GGGGKKRPKPG (SEQ ID NO: 23), RKKRRQRRRGGGGFFFILVF (SEQ ID NO: 24), and GGGGRKKRRQRRR (SEQ ID NO: 25), or any combination thereof and any combination with one or more other efficiency groups described herein.

In particular embodiments, the efficiency groups GGGGKKRPKPG (SEQ ID NO: 23) and/or GGG-GRKKRRQRRR (SEQ ID NO: 25) may be bonded to a palmitoyl group, preferably bonded to n-palmitoyl, to give a lipophilic carrier. Other examples of lipophilic carriers for use in the compositions and methods of the present invention include those selected from the group consisting of palmitoyl-GGRKKRRQRRR (palmitoyl-TAT, SEQ ID NO: 26); palmitoyl-gly$_p$-KKRPKPG (SEQ ID NO: 27); octanoyl-gly$_p$-KKRPKPG (SEQ ID NO: 28), oleyl-gly$_p$-KKRPKPG (SEQ ID NO: 29), or any combination thereof, where p is an integer from 0 to about 20. Still other examples include a lipophilic carrier selected from the group consisting of FFFILVF-gly$_p$-KKRPKPG (SEQ ID NO: 30), FLVFFF-gly$_p$-KKRPKPG (SEQ ID NO: 31), and KKRPKPG-gly$_p$-FLVFFF (SEQ ID NO: 32), or any combination thereof, where p is an integer from 0 to about 10.

Further lipophilic carriers, hydrophobic backbones, and efficiency groups (CPPs) suitable for use in the compositions and methods of the present invention include any described in US 2016/0166703 A1 to Tan et al. "Carrier Molecule Compositions and Related Methods," each of which is incorporated herein by reference in its entirety.

Formulation and Dosage

Compositions of this invention preferably are provided in formulations suitable for application to the luminal surface of the bladder of subjects or patients, i.e. humans or other mammals. In terms of form, compositions of this invention may include solutions, emulsions (including microemulsions), suspensions, or other liquid compositions typically used for instillation to the bladder.

In general, the compositions are prepared by mixing the botulinum toxin with the carrier, and usually with one or more additional pharmaceutically acceptable carriers, diluents, or excipients, preferably sterile and/or otherwise suitable for administration to the bladder lumen. For example, an instillation acceptable excipient, diluent, or carrier may be used, that is, an excipient, diluent, or carrier that is compatible with the bladder tissues to which it will be applied. In some embodiments, a simple aqueous pharmaceutically acceptable carrier, diluent, or excipient may be used, such as sterile buffered saline. Other carriers, diluents, or excipients known for use in bladder instillation also may be used. The compositions further may comprise other ingredients typical for use in instillation, such as antimicrobials, preservatives, solvents, surfactants, viscosity-controlling agents, water, and anesthetics. In preferred embodiments, the compositions of the invention are present in low-viscosity, sterile formulations, suitable for instillation by catheter. The compositions also may include a quantity of a small anion, preferably a monovalent anion, but also may contain polyvalent anions, such as phosphate, aspartate, or citrate.

The vessel used for preparing the mixture may be selected from vessels comprising pharmaceutically suitable process materials (e.g., stainless steel, PETG, polypropylene, polyethylene, vinyl acetate), as well as pharmaceutically acceptable stoppered glass single dose vials (e.g., Schott TopLyo vial) or similarly coated hydrophobic vial (e.g. Schott Type 1 Plus). Unexpectedly, standard borosilicate glass vials that are not hydrophobically treated retain an unacceptable amount of the botulinum toxin in solution, unless the glass vials are first heated to high temperature (e.g., 250° C. for approximately 30 minutes, common for depyrogenation of vials prior to filling).

For preparing a mixture of botulinum toxin and carrier, an adequately clean vessel of appropriate size and of suitable material is selected. The vessel can be filled to about 80% of its target volume with solvent, such as water. Buffer salts (e.g., histidine or sodium phosphate), lyoprotectant (e.g., sucrose, trehalose, or other saccharide), and surfactant (e.g., polysorbate 20) may be added and mixed for at least 1 minute, more preferably for about 10-30 minutes, until all solids are fully dissolved. The composition may be chilled to 2-8° C., and the desired pH confirmed (e.g., pH 6.5 or pH 7.5). In a particular embodiment, carrier RKKRRQRRRG-(K)$_{15}$-GRKKRRQRRR (SEQ ID NO: 7), in the amount of about 75 mcg/mL, and botulinum toxin (e.g., Subtype A, 150 kDa), in the amount of about 5 ng/mL, equivalent to about 800 U/mL, are added and mixed for at least 10 minutes until the components are fully dissolved.

In some embodiments, the compositions for use in the present methods and kits are in the form of controlled-release or sustained-release compositions, which comprise botulinum toxin and the positively charged or lipophilic carrier encapsulated or otherwise contained within a material, such that they are released within the tissue in a controlled manner over time. For example, the composition comprising the botulinum toxin and positively charged or lipophilic carrier may be contained within matrixes, liposomes, vesicles, microcapsules, microspheres and the like, or within a solid particulate material, all of which is selected and/or constructed to provide release of the botulinum toxin over time. The botulinum toxin and the positively charged or lipophilic carrier may be encapsulated together (i.e., in the same capsule) or separately (i.e., in separate capsules).

Compositions of the invention are administered so as to deliver an effective amount of botulinum toxin. The term "effective amount" as used herein refers to a dose of botulinum toxin that brings about at least one therapeutic, desired, or positive benefit, such as reducing, alleviating, decreasing, diminishing, ameliorating, or curing at least one symptom of a bladder disorder or condition in a subject in need thereof. The term effective amount also implies a safe amount, i.e. one that is low enough to avoid serious side effects. In particular embodiments, desired effects include the relaxation of certain muscles of the bladder with the aim of, for instance, reducing spasms or contractions of the bladder wall, or extending the length of intervals between contractions, so as to ultimately decrease a subject's urge to urinate and/or to decrease bladder output and/or leakage. The compositions of the invention generally contain an appropriately effective amount of the botulinum toxin for application as a single-dose treatment, or may be more concentrated, either for dilution at the place of administration or for use in multiple applications. Through the use of the positively charged or lipophilic carriers, as described herein, a botulinum toxin can be delivered transmucosally to a subject for treating bladder disorders and conditions, e.g., conditions which involve undesirable muscular contractility or spasms or undesirable frequency of such contractility or spasms.

Preferably, the compositions are administered by or under the direction of a physician, clinician, medical practitioner, or other health care professional. They may be administered in a single treatment or in a series of periodic treatments over time. Because of its nature, most preferably the amount of botulinum toxin applied should be applied with care, at an application rate and frequency of application that will produce the desired result without or with few serious adverse effects or undesired results that would outweigh the benefits of treatment. Accordingly, for instance, botulinum toxin compositions for instillation should be applied at a rate of from about 0.5 to about 3.5 U, about 0.8 to about 3 U, about 0.84 to about 2.5 U, about 0.9 to about 2.7 U, about 1 to about 2 U, or about 1.5 U of botulinum toxin per $cm^2$ of bladder surface area; in particular, about 0.84 to about 2.5 $U/cm^2$ for men and about 0.9 to about 2.7 $U/cm^2$ for women. Higher dosages within these ranges may be employed, for example, in situations where the botulinum toxin is administered in conjunction with controlled release materials, as described herein.

In certain embodiments, the compositions of the invention are administered as a single dose to a subject or patient in need thereof in an amount (dose) that provides from about 1 to about 15 U/kg, about 3 to about 10 U/kg, about 3.3 to about 10 U/kg, about 4 to about 8 U/kg, about 5 to about 7 U/kg, or about 6.5 U/kg of botulinum toxin for the treatment of a bladder disorder or condition, particularly OAB. Toxin amounts in all values between the foregoing ranges and including the lowest and highest amounts in the range are encompassed. In particular, amounts of botulinum toxin lower than 8,000 U/kg are tolerated based on toxicology studies in rats. Doses are based on considering a 60 kg average body weight for a patient and doses range from about 200-600 U per patient. Other exemplary doses of botulinum toxin for instillation into the bladder include 1 U per kg, 1.5 U per kg, 2 U per kg, 2.5 U per kg, 3 U per kg, 3.5 U per kg, 4 U per kg, 4.5 U per kg, 5 U per kg, 5.5 U per kg, 6 U per kg, 6.5 U per kg, 7 U per kg, 7.5 U per kg, 8 U per kg, 8.5 U per kg, 9 U per kg, 9.5 U per kg, 10 U per kg, 10.5 U per kg, 11 U per kg, 11.5 U per kg, 12 U per kg, 12.5 U per kg, 13 U per kg, 13.5 U per kg, 14 U per kg, 14.5 U per kg, or 15 U per kg, as well as incremental doses therebetween.

In certain embodiments, the compositions of the invention are administered as a single dose to a subject or patient in need thereof in an amount (dose) that provides botulinum toxin for the treatment of a bladder disorder or condition, particularly OAB, from about 0.5 to about 3.5 $U/cm^2$ of bladder surface area, about 0.8 to about 3 $U/cm^2$ of bladder surface area, about 0.84 to about 2.5 $U/cm^2$ of bladder surface area, about 0.9 to about 2.7 $U/cm^2$ of bladder surface area, about 1 to about 2 $U/cm^2$ of bladder surface area, or about 1.5 $U/cm^2$ of bladder surface area; in particular, about 0.84 to about 2.5 $U/cm^2$ of bladder surface area for men and about 0.9 to about 2.7 $U/cm^2$ of bladder surface area for women. Doses are based on considering an average bladder surface area of about 221 $cm^2$ for women and of about 239 $cm^2$ for men; and doses range from about 200-600 U per patient (see, e.g., Kanyilmaz et al., 2013, "Bladder wall thickness and ultrasound estimated bladder weight in healthy adults with portative ultrasound device" *J Res Med Sci.* 18(2):103-106). "Bladder surface area" refers to the surface area of the inner mucosal surface of the luminal bladder wall (the luminal surface of the bladder) of a patient, when the bladder is not extended, for example, after voiding urine. In particular cases, a patient's bladder surface area may be calculated, e.g., using techniques known in the art such as calculating bladder surface area from dimensional measurements obtained from ultrasound scans (see again, e.g., Kanyilmaz et al., 2013) and appropriate dosage determined accordingly.

Stabilized Formulations

Besides enhancing penetration of botulinum toxin, the positively charged carriers described herein have surprisingly been found to also stabilize the botulinum toxin against degradation. The combination of the toxin and the carrier, even in the absence of serum protein, such as human serum albumin, was surprisingly found to essentially completely stabilize toxin activity for at least 3 to 4 hours, more preferably over 8 hours, most preferably at least 5 days.

Accordingly, in another aspect of the invention, the botulinum toxin-containing composition is provided in an aqueous formulation that stabilizes the toxin for at least 3 to 4 hours, more preferably over 8 hours, most preferably at least 5 days. In some embodiments, the stabilized formulation comprises a botulinum toxin, preferably botulinum toxin of serotype A, more preferably of about 150 kDa; a positively charged carrier, preferably a polylysine, more preferably RKKRRQRRRG-$(K)_{15}$-GRKKRRQRRR (SEQ ID NO: 7);

and a non-ionic surfactant, preferably polysorbate 20. In some embodiments, the stabilized formulation further comprises a non-reducing sugar, such as a non-reducing disaccharide or a non-reducing trisaccharide; and/or a physiologically compatible buffer for maintaining the pH between 4.5. and 7.5.

In preferred embodiments, the stabilized formulation requires less foreign accessory proteins (e.g., human serum albumin ranging from 400-600 mg or recombinant serum albumin ranging from 250-500 mg) and/or less polysaccharide stabilizers, affording beneficial reductions in immune responses. In more preferred embodiments, the aqueous formulation is stabilized without a proteinaceous excipient, especially without any animal protein-derived excipients. For example, hemagglutinin protein and/or non-toxin, non-hemagglutinin protein that are normally present to stabilize botulinum toxin may be reduced or omitted entirely from stabilized formulations provided herein. Similarly, exogenous albumin that is normally added during manufacturing may be reduced or omitted entirely from stabilized formulations provided herein.

In particular embodiments, the stabilized formulation comprises a non-ionic surfactant that contributes to stabilizing botulinum toxin and that is suitable for pharmaceutical use. In some embodiments, the non-ionic surfactant is a polysorbate, such as, by way of nonlimiting example, polysorbate 20, polysorbate 40, polysorbate 60, and/or polysorbate 80. In other embodiments, the non-ionic surfactant is a sorbitan ester, non-limiting examples of which include SPAN® 20, SPAN® 60, SPAN® 65, and SPAN® 80. The non-ionic surfactants Triton® X-100 or NP-40 may also be used. In addition, a combination of the different non-ionic surfactants may be used. In certain preferred embodiments, the non-ionic surfactant is a polysorbate, a poloxamer and/or a sorbitan; polysorbates, e.g., polysorbate 20, and sorbitans are particularly preferred. In some embodiments, the non-ionic surfactant is present in the compositions of the invention in the range of about 0.005% to about 0.5%, or in the range of about 0.01% to about 0.2%, or about 0.02% to about 0.1%, or about 0.05 to about 0.08%, inclusive of the upper and lower values. In addition, the compositions of the invention may contain a non-ionic surfactant in the amount of 0.01%, 0.02%, 0.03%, 0.04%, 0.05%, 0.06%, 0.07%, 0.08%, 0.09%, 0.10%, 0.11%, 0.12%, 0.13%, 0.14%, or 0.15%.

In particular embodiments, the stabilized formulation comprises a non-reducing sugar, which is preferably a disaccharide, non-limiting examples of which include trehalose, including its anhydrous and hydrated forms, or sucrose, as well as combinations thereof In some embodiments, the hydrated form of trehalose, trehalose-dihydrate, is preferable. In other embodiments, the compositions comprise a non-reducing a trisaccharide, a non-limiting example of which is raffinose. In general, the concentration of the non-reducing sugar, preferably a disaccharide, e.g., sucrose, in the compositions of the invention are in the range of about 10% to about 40% (w/v), or in the range of about 10% to about 25% (w/v), or in the range of about 15% to about 20% (w/v), inclusive of the upper and lower values. In certain embodiments, the concentration of the non-reducing sugar, preferably a disaccharide, e.g., sucrose, is 10%, 11%, 12%, 13%, 14%, 15%, 16%, 17%, 18%, 19% or 20% (w/v).

Generally, the stabilized formulations further comprise a physiologically compatible buffer capable of maintaining pH in ranges suitable for use, e.g., in the pH range selected from about 4.5 to about 7.5, about 4.5 to about 6.8, and about 4.5 to about 6.5. It is to be understood that a suitable pH also includes the upper and lower pH values in the range. Non-limiting examples of such buffers include salts of citric acid, acetic acid, succinic acid, tartaric acid, maleic acid, and histidine. Non-limiting examples of suitable buffer concentrations include buffer concentrations in the range of about 0.400% to about 0.600%; about 0.450% to about 0.575%, or about 0.500% to about 0.565%. The compositions of the invention may also comprise a mixture of buffer salts, non-limiting examples of which include citrate/acetate, citrate/histidine, citrate/tartrate, maleate/histidine, or succinate/histidine.

Stabilized formulations may be stored either at room temperature or under refrigerated conditions. For example, the stabilized formulation may be held at a temperature of about 2° C.-8° C. In a particular embodiment, stabilized formulations described herein are suitable for the preparation of a liquid bulk drug product, which remains stable and retains toxin activity for more than four hours and up to about 5 days (prior to lyophilization). The stabilized formulation thus allows time to work with the product, for example, in completing "fill finish" manufacturing processes involved in manufacture of finished dosage forms, without the need to include human serum albumin having associated risks.

Aqueous formulations of the toxin and/or carrier, including stabilized formulations described herein, may be dried, preferably by lyophilization, to produce stabilized solid forms. Preferably, the dried, e.g., lyophilized, solid forms are noncrystalline and amorphous solid compositions, for example, amorphous powders. In preferred embodiments, the stabilized solid forms do not include animal protein-derived products, such as albumin or human serum albumin.

The lyophilized form may be reconstituted prior to use with sterile buffered saline, a pharmaceutically acceptable aqueous buffer, or other pharmaceutically acceptable excipient, diluent, or carrier suitable for bladder instillation, as described above.

Kits

Another aspect of the invention provides kits for use with the compositions and methods described herein. In some embodiments, the kit provides one or more compositions or formulations described herein for use in a method of the invention. For example, kits may provide a botulinum toxin and/or a positively charged or lipophilic carrier and/or a device to facilitate topical administration of the toxin in conjunction with the carrier to the luminal surface of the bladder for transdermal delivery through the luminal mucosal surface.

Generally, the compositions are pre-formulated and/or pre-installed in a device, or can be prepared later, for example, prior to use. In some embodiments, a kit is provided that houses the botulinum toxin and carrier separately, but provides means for combining them at or prior to the time of application. The amount of carrier or the ratio of it to the botulinum toxin will depend on which carrier is chosen for use in the composition in question. The appropriate amount or ratio of carrier in a given case can readily be determined, for example, by conducting one or more experiments, such as those described below. In some embodiments, the kit provides a pre-formulated composition of the toxin and carrier, preferably wherein the toxin is in direct, non-covalent association with the carrier.

In some embodiments, the kit further or instead contains a device for topically administering the toxin and carrier components separately, or for topically administering a composition comprising toxin and carrier. The device may be any of the installation devices described above for carrying out methods of the invention. In preferred embodiments, the kit provides both a device for dispensing botulinum toxin via instillation and a solution containing the carrier and/or toxin and that also is suitable for instillation. Kits for administering the compositions of the inventions, either under direction of a health care professional or by the patient or subject, may also include instructions for use.

In some embodiments, the kit provides a stabilized formulation of the toxin, such as formulations comprising the toxin and a positively-charged carrier, as described herein. In some embodiments, the toxin is provided in lyophilized form for reconstitution at point of use. In preferred embodiments, the kit further includes a sterile, pharmaceutically acceptable buffer suitable for instillation and for use in reconstitution. The kit may still further include a device facilitating reconstitution and/or instillation of the reconstituted solution. The installation device may be a standard urethral catheter such as, for example, BARDEX® I.C., 2-way catheter, part #0165SI14 Balloon 5 cc, 14FR latex; Foley Catheters, LUBRI-SIL®, 2-way, part #175814 Balloon 5 cc, 14FR silicone; Coloplast 14 fr catheter: SELF-CATH® part number: 450, 14 FR Uncoated, HCPCS code: A4351, and 16 inch PVC Straight Tip 50, as well as any other instillation devices known in the art or described herein.

In some embodiments, lyophilized botulinum toxin is pre-loaded into a reconstitution/instillation device. The medical professional then follows a reconstitution process and further dilution to prepare the installation solution for administration. The dose is then instilled as described herein and/or as known in the art.

Advantages of the Transmucosal Compositions, Methods, and Kits

The compositions, kits, and methods described herein provide benefits and advantages over other compositions and methods in which neurotoxin is administered to the bladder using injection, as well as advantages over compositions and methods using, e.g., a liposomal formulations, DMSO, and/or only saline. In order to attain a therapeutic effect, such treatments frequently require pre-treatment of the bladder lining with protamine to remove or alter the integrity of the bladder lining, which can cause inflammation and pain to the subject. In contrast, the methods of the invention do not require a protamine stripping procedure. Furthermore, the present compositions, kits, and methods need not include liposomes (as described in, e.g., WO 2012/0093920 and WO 2009/139984 to Lipella Pharmaceuticals, Inc.); nor a sustained-release poloxamer (as described in, e.g., WO 2009/105369 to Allergan, Inc.); nor extracellular matrix-digesting enzymes (as described in, e.g., WO 2008/101098 to Allergan, Inc.); nor DMSO (as described in, e.g., WO 2008/030638 to Mayo Foundation and Petrou S. et al, 2009, *Mayo Clin Proc*, 84(8):702-6), each of which is incorporated herein in its entirety.

The present methods also may provide for longer duration of effect compared to injection methods and/or other instillation approaches. For example, intravesical installation of botulinum toxin with DMSO in a Phase 1/2 study failed to provide significant improvement in refractory indiopathic detrusor overactivitiy patients, with symptoms returning to baseline within 3 months (Petrou S. et al, 2009, *Mayo Clin Proc*, 84(8):702-6). In some embodiments, the present methods provide for longer duration of effect, resulting in improved and prolonged efficacy in the treatment of bladder disorders or conditions, such as OAB. In preferred embodiments, following a single administration of the composition to a subject or patient, a desired effect, such as reduction of OAB and/or a decrease in bladder hypercontractility, endures for several weeks or months, for example, for at least 2, 3, 4, 5, 6, 7, 8, 9, 10, 11, 12, 13, 14, 15, 16, 17, 18, 19, or 20 weeks, or for at least 1, 2, 3, 4, 5, 6 months, or greater than 6 months, such as 6, 7, 8, 9, or 10 months, or longer. Accordingly, in such preferred embodiments, a single treatment with an effective dose of the described compositions affords an effect of long duration, thus requiring fewer administrations during a single treatment session, and/or a longer interval between sessions.

Moreover, the present methods offer far less painful and significantly less invasive treatments compared with methods injecting the toxin into the bladder wall, often at multiple sites, using a transurethral cystoscope. As discussed above, injection procedures typically are more invasive, painful, expensive, burdensome, and labor intensive, as well as requiring more specialized medical training to perform. Also as noted above, the present compositions, kits, and methods provide more complete treatment of the entire interior wall of the bladder, due to more even and thorough distribution of toxin across the bladder wall, rather than relying on regional injections, using a cytoscope, where the injections are localized to a smaller portion of the bladder wall. Accordingly, the present compositions, kits, and methods provide greater efficacy and improved safety compared with injection and cystoscopic methods.

According to the present invention, the positively charged or lipophilic carrier surprisingly can serve as a transport system for botulinum toxin in the context of urothelial transmucosal delivery across the unique mucosa of the inner lining of the bladder, enabling the toxin to be topically administered and transmucosally delivered via penetration to surrounding structures, such as the bladder muscles and neuronal tissue.

It will be understood that the following examples and embodiments described herein are for illustrative purposes and that various modifications or changes in light thereof will be suggested to persons skilled in the art and are to be included within the spirit and purview of this application and scope of the appended claims.

All publications, patents, and published patent applications cited herein are hereby incorporated by reference in their entireties for all purposes.

EXAMPLES

Example 1

Bladder Contractility Assessment Following a Single Intravesical Instillation of Botulinum Toxin A for Treatment of Overactive Bladder in Female Sprague-Dawley Rats This Example describes a study conducted to confirm the feasibility of intra-bladder instillation and to investigate the efficacy of a test composition to reduce overactive bladder (OAB) in a model of OAB in female Sprague Dawley rats. To model OAB, bladder hyperactivity was induced by instillation of acetic acid into the animal's bladder. The test composition used was an exemplary, stable composition ("RT003"), containing purified botulinum toxin A of 150 kDa and the positively charged carrier RKKRRQRRRG-(K)$_{15}$-GRKKRRQRRR (SEQ ID NO: 7), as described in Example 2, below.

The animals used were Sprague Dawley female rats (Charles River, Canada), about 8-9 weeks old and about 215 to 370 grams in weight.

The study design involved three phases. The first phase (Phase 1) was carried out to establish bladder hyperactivity in the animals using 0.3% acetic acid and served as a non-treatment control. The animals (n=5) first underwent cystometry during intravesical instillation of saline to provide baseline values, in accordance with the procedures below.

Bladder instillation: The animals were anesthetized using isoflurane prior to catheterization. A temporary catheter was inserted into the bladder via the urethra of the animal using an aseptic technique. The catheter was tied in position with a ligature around the urethral meatus. The bladder was drained (emptied) using a syringe or by gentle palpation of the bladder and prewashed with preservative-free sterile saline. 0.5 mL of preservative-free sterile saline was then instilled into the bladder via the catheter. After a dwell time of 60 minutes, the bladder contents were removed via the catheter and the bladder was washed again with preservative-free sterile saline. The catheter was then removed.

Cystometry: For cystometry, the catheter was connected with 3-way stopcock to a pressure transducer and a syringe pump. Intravesical pressure was recorded during infusion of solution into the bladder. For example, when measuring baseline values, the bladder was filled with saline using an infusion pump at a rate of 0.08 ml/min and was monitored for repetitive contractions. Measurements were taken over at least 5 complete cycles of bladder contractions. The following parameters were monitored over the 5 cycles (bladder contractions) at each occasion (baseline and OAB): pressure amplitude (peak minus baseline); pressure baseline, with empty bladder or after reflex contraction; and inter-contractile interval, i.e., average time between contractions.

One week later, the animals received intravesical instillation with 0.3% acetic acid, to induce overactive bladder, following a similar procedure, and again underwent cystometry, also as described above.

Phase 2 was conducted as a dose-range finding segment of the study and evaluated efficacy of the test composition. Female rats were assigned to 2 groups (n=5 per group) that received 0.5 ml of RT003, providing either 10 U/animal or 100 U/animal, by intravesical instillation with an approximately 1 hour-retention time. Animals underwent the same cystometry procedures for measuring bladder contractility, at baseline and upon induction of OAB, as described with respect to Phase 1.

Specifically, one day following baseline cystometry, the animals were dosed according to their group. One week post-dosing, OAB was established as described above, that is, 0.3% acetic acid was infused at a rate of 0.08 ml/min, inducing acute bladder hyperactivity over 30 minutes. Cystometry was conducted as described above. The data obtained in Phase 2 were used to select dose levels of RT003 for use in Phase 3. Due to significant inter-individual variations in bladder contractility, the number of animals was increased to n=10/group during the next study phase.

In Phase 3, female rats received a 0.5 ml intravesical instillation of saline (as a control) or RT003, at either 3 or 30 units/animal, with 1 hour-retention in the bladder, at least one day after baseline cystometry. OAB was induced one week after dosing, as described with respect to Phase 1 or 2, and cystometry performed, again as described above.

Dosing and cystometry were performed under inhalant gas anesthesia using isoflurane during all phases of the study. Further, in addition to the assessment of bladder contractility, other parameters were assessed throughout the study, including mortalities, clinical signs, food consumption, and body weight. All animals were euthanized on Day 7 without any post-mortem investigation.

Figure 2:
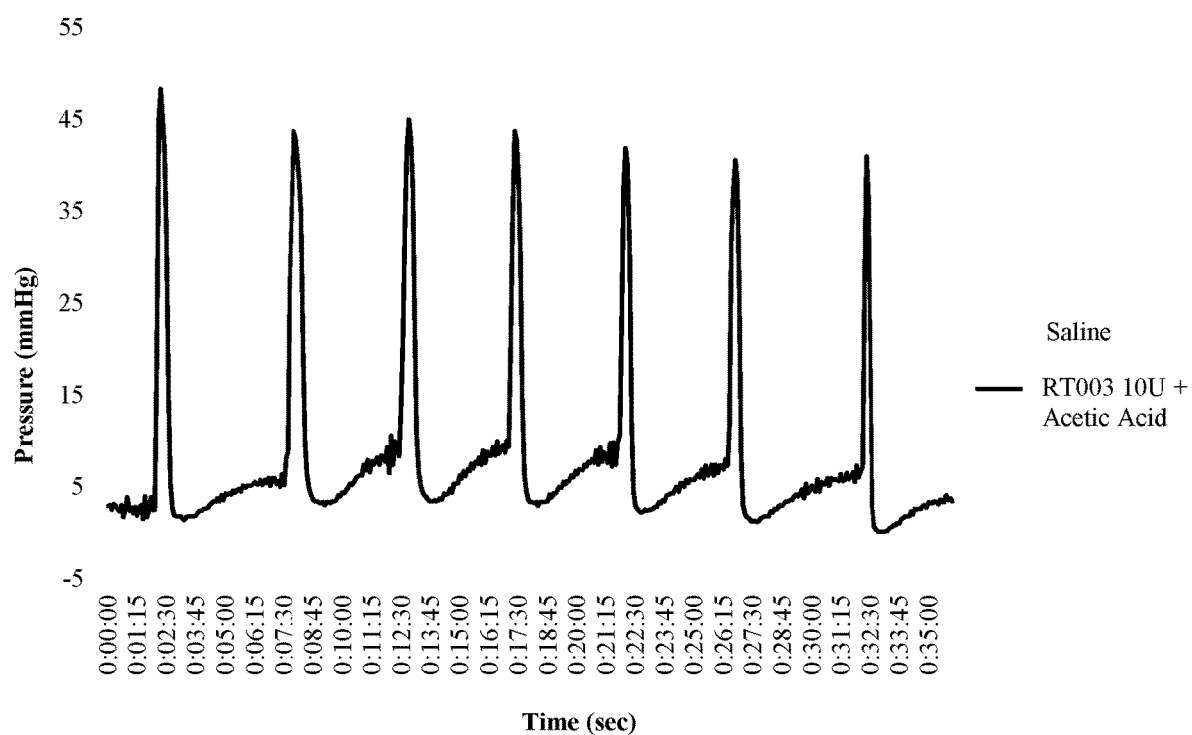
FIG. 2 depicts representative results showing the number of contractions in the bladder of a rat treated with RT003 (10 U/animal); baseline contractions are shown in grey lines and acetic acid-induced hypercontractility is shown in black lines. The interval between contractions under acetic acid treatment is much longer compared to that of the saline-treated control animal (FIG. 1) and is similar to the baseline interval prior to acetic acid treatment, indicating resolution of the hypercontractile disease state by instillation of 10 U of RT003.
Figure 3:
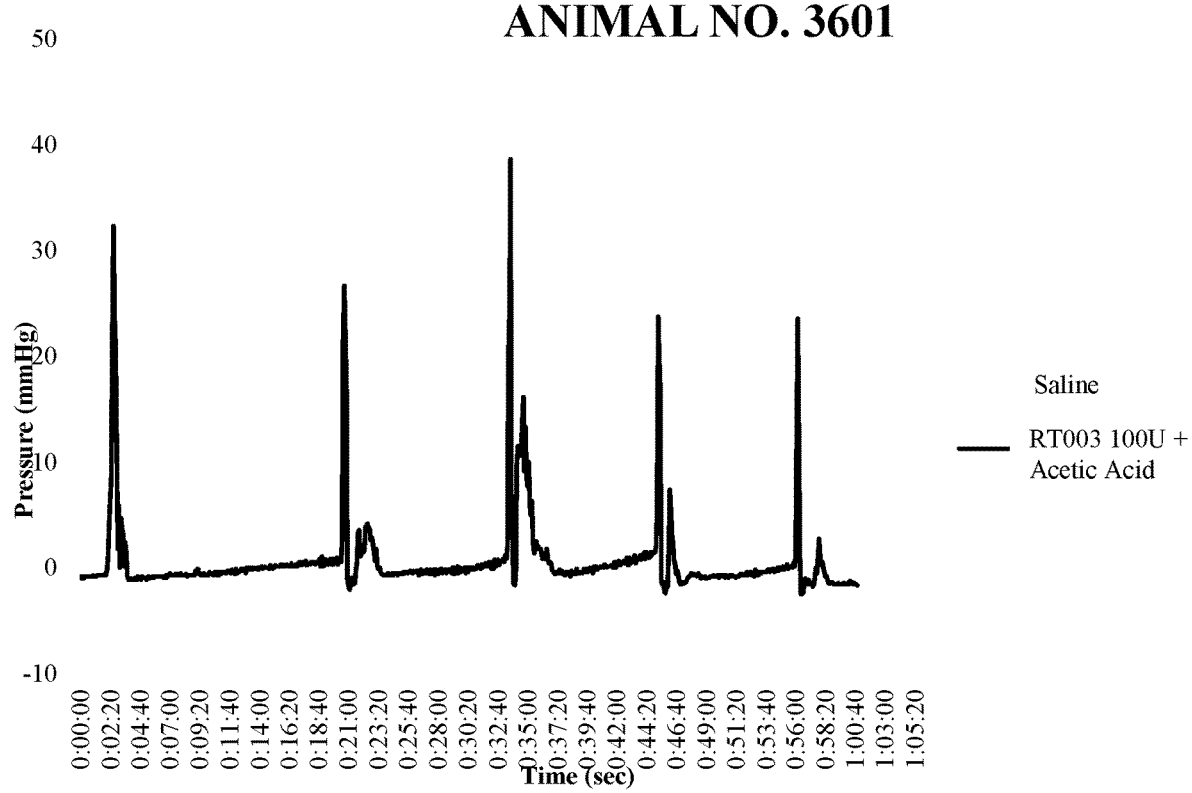
FIG. 3 depicts representative results showing the number of contractions in the bladder of a rat treated with RT003 (100 U/animal); baseline contractions are shown in grey lines and acetic acid-induced hypercontractility is shown in black shading. The interval between contractions under acetic acid treatment is much longer compared to that of the saline-treated control animal (FIG. 1) and is similar to the baseline interval prior to acetic acid treatment, indicating resolution of the hypercontractile disease state by instillation of 100 U of RT003.

Results: Results are provided in FIG. 1 (control), FIG. 2 (RT003 at 10 U/rat), and FIG. 3 (RT003 at 100 U/rat). Comparing the figures, it can be seen that the interval between contractions under acetic acid treatment (i.e., mimicking OAB) is much longer compared to that of control animals and is similar to the baseline interval prior to acetic acid treatment, thus indicating resolution of the hypercontractile disease state. Further, the results demonstrated a dose response of decreasing hypercontractility and resolution towards baseline contractility as a result of the increasing dose (i.e., 10 U versus 100 U RT003) as compared to control (saline-treated) animals, receiving no RT003.

Clinical signs related to the test composition were limited to one animal that had received 100 units. The clinical signs included decreased appetite, hunched back posture, decreased activity level, and slight weight loss. Improvement was noted after fluid therapy and nutritional support were provided. In addition, no significant RT003-related adverse effects were noted in body weight or food consumption at any dose levels. There also were no mortalities during the study.

Figure 4:
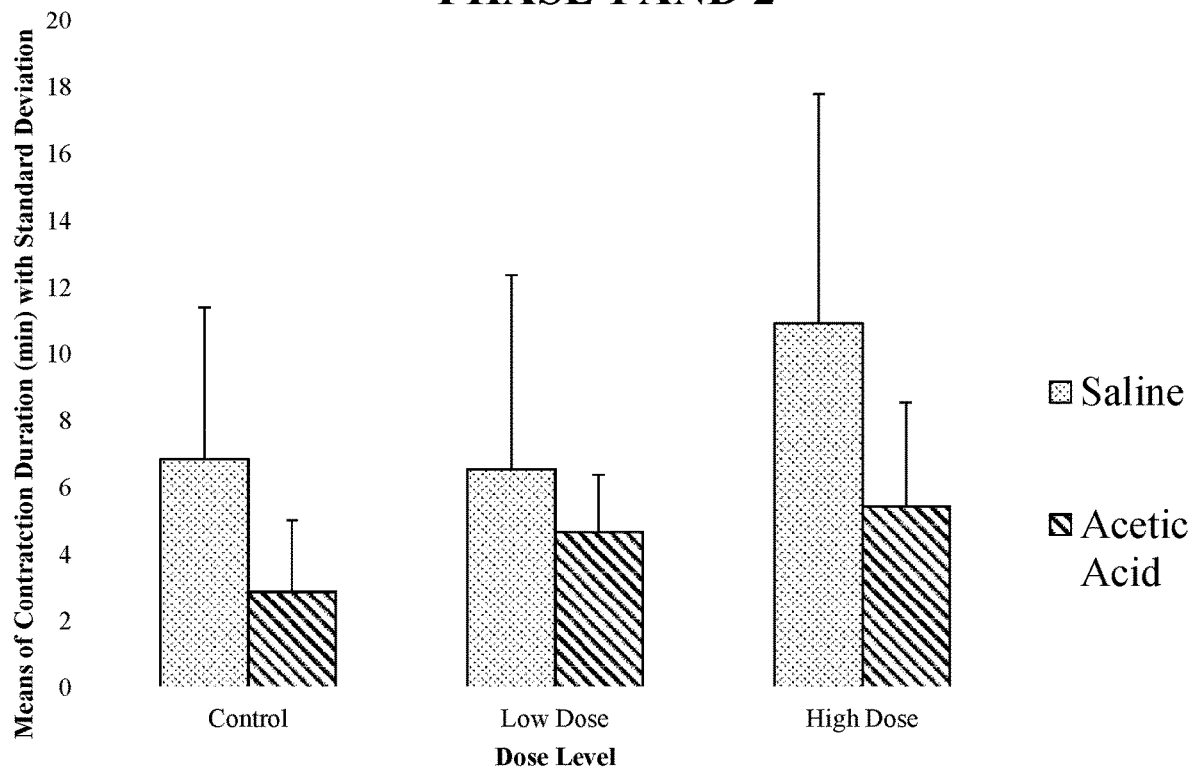
FIG. 4 depicts a summary of the mean duration of contraction of untreated (control) rats and RT003-treated rats at Low (10 U/rat) or High (100 U/rat) RT003 doses, at baseline, using saline (dotted shading) and following induction of hypercontractility with acetic acid (solid shading). There is a dose response of decreasing hypercontractility and resolution towards baseline contractility as a result of increasing the dose of RT003, as compared to controls that received no RT003.

In sum, intravesical instillation of 0.3% acetic acid induced OAB and significantly decreased inter-contraction interval in control animals (e.g., in Phase 1 and Phase 3), confirming efficacy of the procedure for inducing bladder hyperactivity in this animal model. Administration of RT003 was associated with mild to moderate reduction in OAB symptoms, as measured by cystometry in Phase 2 and Phase 3, reflected in increased inter-contraction intervals, by +15% to +86% (see FIG. 4).

Example 2

Preparation of Botulinum Toxin-Containing Compositions

This Example provides an illustrative procedure for the preparation of a composition containing botulinum toxin and a positively charged peptide carrier. An adequately clean vessel of appropriate size was filled to 80% of target volume with water. Histidine buffer, sucrose (as lyoprotectant), and polysorbate 20 (as surfactant) were added and mixed for about 10-30 minutes until all solids are fully dissolved. The composition was chilled to 2-8° C., and the pH of 6.5 was confirmed. Carrier RKKRRQRRRG-(K)$_{15}$-GRKKRRQRRR (SEQ ID NO: 7) in the amount of 75 mcg/mL, and botulinum toxin (Subtype A, 150 kDa), in the amount of 5 ng/mL, were added and mixed for at least 10 minutes until the components were fully dissolved.

What is claimed is:

1. A method of treating a bladder disorder or condition in a subject in need thereof, the method comprising administering to a luminal surface of the bladder of the subject an effective amount of a composition comprising a botulinum toxin in conjunction with a carrier, said carrier comprising a backbone having covalently attached thereto one or more cell penetrating peptides,
wherein said carrier is a positively charged carrier with the backbone being a positively charged polymeric backbone or a lipophilic carrier with the backbone being a hydrophobic oligomeric or polymeric backbone;
wherein the botulinum toxin is delivered transmucosally via a balloon catheter in an effective amount for treating the subject's bladder disorder or condition,
wherein a balloon end of the balloon catheter is comprised of an inner balloon configured to inflate to occupy the lumen of the bladder and an outer sheath disposed over the inner balloon, having regularly spaced holes, and configured for administration of the composition to the luminal surface through the holes.

2. A method of increasing bladder contraction intervals associated with a hypercontractility bladder disorder or condition in a subject in need thereof, the method comprising administering to a luminal surface of the bladder of the subject an effective amount of a composition comprising a botulinum toxin in conjunction with a carrier, said carrier comprising a backbone having covalently attached thereto one or more cell penetrating peptides,
wherein said carrier is a positively charged carrier with the backbone being a positively charged polymeric backbone;
wherein the botulinum toxin is delivered transmucosally in an effective amount for treating the subject's bladder disorder or condition,
wherein a balloon end of the balloon catheter is comprised of an inner balloon configured to inflate to occupy the lumen of the bladder and an outer sheath disposed over the inner balloon, having regularly spaced holes, and configured for administration of the composition to the luminal surface through the holes.

3. The method according to claim 1, wherein administration of the composition decreases bladder hypercontractility in the subject, thereby increasing bladder contraction intervals.

4. The method according to claim 1, wherein the bladder disorder or condition is selected from overactive bladder (OAB) or bladder hyperactivity, urge incontinence due to overactive detrusor activity, idiopathic urge incontinence, interstitial cystitis, and bladder pain syndrome.

5. The method for use according to claim 4, wherein the bladder disorder or condition is overactive bladder (OAB) or bladder hyperactivity.

6. The method for use according to claim 4, wherein the bladder disorder or condition is urge incontinence due to overactive detrusor activity.

7. The method for use according to claim 4, wherein the bladder disorder or condition is idiopathic urge incontinence.

8. The method for use according to claim 4, wherein the bladder disorder or condition is interstitial cystitis.

9. The method for use according to claim 4, wherein the bladder disorder or condition is bladder pain syndrome.

10. The method for use according to claim 1, wherein the botulinum toxin and the positively charged or lipophilic carrier are formulated in the composition, wherein the botulinum toxin directly associates with the carrier to form a non-covalent complex.

11. The method according to claim 1, wherein the carrier is the positively charged carrier.

12. The method according to claim 11, wherein the cell penetrating peptides of the positively charged carrier are selected from amino acid sequences -(gly)n1-(arg)n2(SEQ ID NO. 1), wherein n1 is an integer of from 0 to about 20, and n2 is independently an odd integer of from about 5 to about 25; (gly)p-RGRDDRRQRRR- (gly)q (SEQ ID NO. 2); (gly)p-YGRKKRRQRRR-(gly)q (SEQ ID NO. 3);
and (gly)p-RKKRRQRRR-(gly)q (SEQ ID NO. 4), wherein p and q are each independently an integer of from 0 to about 20.

13. The method according to claim 12, wherein the one or more positively charged efficiency groups have the amino acid sequence -(gly)n1- (arg)n2 (SEQ ID NO. 1), wherein n1 is an integer of from about 0 to about 20 and n2 is independently an odd integer of from about 5 to about 25.

14. The method according to claim 12, wherein n1 is an integer of from 0 to about 8.

15. The method according to claim 12, wherein n2 is an odd integer of from about 7 to about 17.

16. The method according to claim 12, wherein the cell penetrating peptides are selected from (gly)p-RGRDDRRQRRR-(gly)q (SEQ ID NO. 2), (gly)p-YGRKKRRQRRR-(gly)q (SEQ ID NO. 3), or (gly)p-RKKRRQRRR-(gly)q (SEQ ID NO. 4), wherein p and q are each independently an integer of from 0 to about 20.

17. The method according to claim 12, wherein p and q are each independently an integer of from about 2 to about 5.

18. The method according to claim 12, wherein the one or more cell penetrating peptide are attached to either end, or both ends, of the positively charged backbone of the positively charged carrier.

19. The method according to claim 1, wherein the positively charged backbone comprises a positively charged polypeptide.

20. The method according to claim 19, wherein the positively charged polypeptide comprises a polylysine from about 5 to about 50 lysine residues.

21. The method according to claim 12, wherein the positively charged carrier comprises the amino acid sequence (G)p-RKKRRQRRR-(G)q- (K)n-(G)q-RKKRRQRRR -(G)p (SEQ ID NO: 8), wherein p is an integer of from 0 to 2, q is an integer of from 0 to 2, and n is an integer of from about 10 to about 20.

22. The method according to claim 21, wherein p is 0, q is 1, and n is from 10 to 20.

23. The method according to claim 22, wherein the positively charged carrier is the amino acid sequence RKKRRQRRRG-(K)15-GRKKRRQRRR (SEQ ID NO: 7).

24. The method according to claim 1, wherein the carrier comprises said lipophilic carrier.

25. The method according to claim 24, wherein the cell penetrating peptides are selected from the group consisting of KKRPKPGGGGFFFILVF (SEQ ID NO: 21), FFFIL-VFGGGKKRPKPG (SEQ ID NO: 22), GGGGKKRPKPG (SEQ ID NO: 23), RKKRRORRRGGGGFFFILVF (SEQ ID NO: 24), and GGGGRKKRRQRRR (SEQ ID NO: 25).

26. The method according to claim 24, wherein said lipophilic carrier is selected from the group consisting of palmitoyl- GGRKKRRQRRR (palmitoyl-TAT, SEQ ID NO: 26) and palmitoyl-glyp-KKRPKPG (SEQ ID NO: 27).

27. The method according to claim 24, wherein the composition is contained in liposomes.

28. The method according to claim 1, wherein the botulinum toxin is serotype A.

29. The method according to claim 1, wherein the botulinum toxin is administered in an amount of about 1 U/kg to about 15 U/kg or about 0.5 to U/cm$^2$ about 3.5 U/cm$^2$.

30. The method according to claim 1, wherein the composition does not contain human serum albumin.

31. A kit comprising
a composition comprising a botulinum toxin and
a carrier comprising a backbone having covalently attached thereto one or more positively charged efficiency groups, wherein said carrier is a positively charged carrier with the backbone being a positively charged polymeric backbone; and
a balloon catheter, wherein a balloon end of the balloon catheter is comprised of an inner balloon configured to inflate to occupy the lumen of the bladder and an outer sheath disposed over the inner balloon, having regularly spaced holes, and configured for administration of the composition to the luminal surface through the holes.

* * * * *

SEQUENCE LISTING

<160> NUMBER OF SEQ ID NOS: 33

<210> SEQ ID NO 1
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(20)
<223> OTHER INFORMATION: This region may encompass 0-20 residues
<220> FEATURE:
<221> NAME/KEY: MISC_FEATURE
<222> LOCATION: (21)..(45)
<223> OTHER INFORMATION: This region may encompass 5, 7, 9, 11, 13, 15,
      17, 19, 21, 23, or 25 residues
<220> FEATURE:
<223> OTHER INFORMATION: See specification as filed for detailed
      description of substitutions and preferred embodiments

<400> SEQUENCE: 1

Gly Gly Gly Gly Gly Gly Gly Gly Gly Gly Gly Gly Gly Gly Gly
1               5                   10                  15

Gly Gly Gly Gly Arg Arg Arg Arg Arg Arg Arg Arg Arg Arg Arg
            20                  25                  30

Arg Arg Arg Arg Arg Arg Arg Arg Arg Arg Arg Arg Arg
        35                  40                  45

<210> SEQ ID NO 2
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(20)
<223> OTHER INFORMATION: This region may encompass 0-20 residues
<220> FEATURE:
<221> NAME/KEY: MISC_FEATURE
<222> LOCATION: (32)..(51)
<223> OTHER INFORMATION: This region may encompass 0-20 residues
<220> FEATURE:
<223> OTHER INFORMATION: See specification as filed for detailed
      description of substitutions and preferred embodiments

<400> SEQUENCE: 2

Gly Gly Gly Gly Gly Gly Gly Gly Gly Gly Gly Gly Gly Gly Gly
1               5                   10                  15

Gly Gly Gly Gly Arg Gly Arg Asp Asp Arg Arg Gln Arg Arg Arg Gly
            20                  25                  30

Gly Gly Gly Gly Gly Gly Gly Gly Gly Gly Gly Gly Gly Gly Gly
        35                  40                  45

Gly Gly Gly
    50

<210> SEQ ID NO 3
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(20)

```
<223> OTHER INFORMATION: This region may encompass 0-20 residues
<220> FEATURE:
<221> NAME/KEY: MISC_FEATURE
<222> LOCATION: (32)..(51)
<223> OTHER INFORMATION: This region may encompass 0-20 residues
<220> FEATURE:
<223> OTHER INFORMATION: See specification as filed for detailed
      description of substitutions and preferred embodiments

<400> SEQUENCE: 3

Gly Gly Gly Gly Gly Gly Gly Gly Gly Gly Gly Gly Gly Gly Gly Gly
1               5                   10                  15

Gly Gly Gly Gly Tyr Gly Arg Lys Lys Arg Arg Gln Arg Arg Arg Gly
            20                  25                  30

Gly Gly Gly Gly Gly Gly Gly Gly Gly Gly Gly Gly Gly Gly Gly
        35                  40                  45

Gly Gly Gly
    50

<210> SEQ ID NO 4
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(20)
<223> OTHER INFORMATION: This region may encompass 0-20 residues
<220> FEATURE:
<221> NAME/KEY: MISC_FEATURE
<222> LOCATION: (30)..(49)
<223> OTHER INFORMATION: This region may encompass 0-20 residues
<220> FEATURE:
<223> OTHER INFORMATION: See specification as filed for detailed
      description of substitutions and preferred embodiments

<400> SEQUENCE: 4

Gly Gly Gly Gly Gly Gly Gly Gly Gly Gly Gly Gly Gly Gly Gly Gly
1               5                   10                  15

Gly Gly Gly Gly Arg Lys Lys Arg Arg Gln Arg Arg Arg Gly Gly
            20                  25                  30

Gly Gly Gly Gly Gly Gly Gly Gly Gly Gly Gly Gly Gly Gly Gly
        35                  40                  45

Gly

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Gly Arg Arg Arg Arg Arg Arg Arg
1               5                   10

<210> SEQ ID NO 6
<211> LENGTH: 19
<212> TYPE: PRT
<213> ORGANISM: Drosophila sp.
```

```
<400> SEQUENCE: 6

Ser Gly Arg Gln Ile Lys Ile Trp Phe Gln Asn Arg Arg Met Lys Trp
1               5                   10                  15

Lys Lys Cys

<210> SEQ ID NO 7
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Arg Lys Lys Arg Arg Gln Arg Arg Gly Lys Lys Lys Lys Lys
1               5                   10                  15

Lys Lys Lys Lys Lys Lys Lys Lys Gly Arg Lys Lys Arg Arg Gln
            20                  25                  30

Arg Arg Arg
        35

<210> SEQ ID NO 8
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(2)
<223> OTHER INFORMATION: This region may encompass 0-2 residues
<220> FEATURE:
<221> NAME/KEY: MISC_FEATURE
<222> LOCATION: (12)..(13)
<223> OTHER INFORMATION: This region may encompass 0-2 residues
<220> FEATURE:
<221> NAME/KEY: MISC_FEATURE
<222> LOCATION: (14)..(33)
<223> OTHER INFORMATION: This region may encompass 10-20 residues
<220> FEATURE:
<221> NAME/KEY: MISC_FEATURE
<222> LOCATION: (34)..(35)
<223> OTHER INFORMATION: This region may encompass 0-2 residues
<220> FEATURE:
<221> NAME/KEY: MISC_FEATURE
<222> LOCATION: (45)..(46)
<223> OTHER INFORMATION: This region may encompass 0-2 residues
<220> FEATURE:
<223> OTHER INFORMATION: See specification as filed for detailed
      description of substitutions and preferred embodiments

<400> SEQUENCE: 8

Gly Gly Arg Lys Lys Arg Arg Gln Arg Arg Gly Gly Lys Lys Lys
1               5                   10                  15

Lys Lys Lys Lys Lys Lys Lys Lys Lys Lys Lys Lys Lys Lys Lys
            20                  25                  30

Lys Gly Gly Arg Lys Lys Arg Arg Gln Arg Arg Arg Gly Gly
        35                  40                  45

<210> SEQ ID NO 9
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 9

Tyr Gly Arg Lys Lys Arg Arg Gln Arg Arg Gly Lys Lys Lys Lys
1               5                   10                  15

Lys Lys Lys Lys Lys Lys Lys Lys Lys Lys Gly Tyr Gly Arg Lys
                20                  25                  30

Lys Arg Arg Gln Arg Arg Arg
            35

<210> SEQ ID NO 10
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Arg Gly Arg Asp Asp Arg Arg Gln Arg Arg Gly Lys Lys Lys Lys
1               5                   10                  15

Lys Lys Lys Lys Lys Lys Lys Lys Lys Lys Gly Arg Gly Arg Asp
                20                  25                  30

Asp Arg Arg Gln Arg Arg Arg
            35

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Leu Ala Lys Leu Ala Lys
1               5

<210> SEQ ID NO 12
<211> LENGTH: 7
<212> TYPE: PRT
<213> ORGANISM: Unknown
<220> FEATURE:
<223> OTHER INFORMATION: Description of Unknown:
      Efficiency group sequence

<400> SEQUENCE: 12

Lys Lys Arg Pro Lys Pro Gly
1               5

<210> SEQ ID NO 13
<211> LENGTH: 12
<212> TYPE: PRT
<213> ORGANISM: Unknown
<220> FEATURE:
<223> OTHER INFORMATION: Description of Unknown:
      Prion sequence

<400> SEQUENCE: 13

Ala Ala Val Leu Leu Pro Val Leu Leu Ala Ala Pro
1               5                   10

<210> SEQ ID NO 14
<211> LENGTH: 9
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 14

Arg Arg Arg Arg Arg Arg Arg Arg
1               5

<210> SEQ ID NO 15
<211> LENGTH: 15
<212> TYPE: PRT
<213> ORGANISM: Drosophila sp.

<400> SEQUENCE: 15

Arg Gln Ile Lys Trp Phe Gln Asn Arg Arg Met Lys Trp Lys Lys
1               5                   10                  15

<210> SEQ ID NO 16
<211> LENGTH: 38
<212> TYPE: PRT
<213> ORGANISM: Unknown
<220> FEATURE:
<223> OTHER INFORMATION: Description of Unknown:
      Transduction Domain 1 sequence

<400> SEQUENCE: 16

Asn Pro Gly Gly Tyr Cys Leu Thr Lys Trp Met Ile Leu Ala Ala Glu
1               5                   10                  15

Leu Lys Cys Phe Gly Asn Thr Ala Val Ala Lys Cys Asn Val Asn His
            20                  25                  30

Asp Ala Glu Phe Cys Asp
        35

<210> SEQ ID NO 17
<211> LENGTH: 26
<212> TYPE: PRT
<213> ORGANISM: Unknown
<220> FEATURE:
<223> OTHER INFORMATION: Description of Unknown:
      Melittin sequence

<400> SEQUENCE: 17

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 18
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(20)
<223> OTHER INFORMATION: This region may encompass 0-20 residues
<220> FEATURE:
<221> NAME/KEY: MISC_FEATURE
<222> LOCATION: (28)..(47)
<223> OTHER INFORMATION: This region may encompass 0-20 residues
<220> FEATURE:
<223> OTHER INFORMATION: See specification as filed for detailed
      description of substitutions and preferred embodiments
```

-continued

<400> SEQUENCE: 18

Gly Gly Gly Gly Gly Gly Gly Gly Gly Gly Gly Gly Gly Gly Gly
1               5                   10                  15

Gly Gly Gly Gly Lys Lys Arg Pro Lys Pro Gly Gly Gly Gly Gly
            20                  25                  30

Gly Gly Gly Gly Gly Gly Gly Gly Gly Gly Gly Gly Gly
        35                  40                  45

<210> SEQ ID NO 19
<211> LENGTH: 8
<212> TYPE: PRT
<213> ORGANISM: Unknown
<220> FEATURE:
<223> OTHER INFORMATION: Description of Unknown:
      Efficiency group sequence

<400> SEQUENCE: 19

Phe Leu Val Phe Phe Phe Gly Gly
1               5

<210> SEQ ID NO 20
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(20)
<223> OTHER INFORMATION: This region may encompass 0-20 residues
<220> FEATURE:
<221> NAME/KEY: MISC_FEATURE
<222> LOCATION: (28)..(47)
<223> OTHER INFORMATION: This region may encompass 0-20 residues
<220> FEATURE:
<223> OTHER INFORMATION: See specification as filed for detailed
      description of substitutions and preferred embodiments

<400> SEQUENCE: 20

Gly Gly Gly Gly Gly Gly Gly Gly Gly Gly Gly Gly Gly Gly Gly
1               5                   10                  15

Gly Gly Gly Gly Lys Lys Arg Pro Gln Pro Asp Gly Gly Gly Gly
            20                  25                  30

Gly Gly Gly Gly Gly Gly Gly Gly Gly Gly Gly Gly Gly
        35                  40                  45

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Lys Lys Arg Pro Lys Pro Gly Gly Gly Gly Phe Phe Phe Ile Leu Val
1               5                   10                  15

Phe

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 22

Phe Phe Phe Ile Leu Val Phe Gly Gly Lys Lys Arg Pro Lys Pro
1               5                  10                  15

Gly

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Gly Gly Gly Lys Lys Arg Pro Lys Pro Gly
1               5                  10

<210> SEQ ID NO 24
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Lys Lys Arg Arg Gln Arg Arg Gly Gly Gly Gly Phe Phe Phe
1               5                  10                  15

Ile Leu Val Phe
            20

<210> SEQ ID NO 25
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Gly Gly Gly Arg Lys Lys Arg Arg Gln Arg Arg
1               5                  10

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term palmitoyl

<400> SEQUENCE: 26

Gly Gly Arg Lys Lys Arg Arg Gln Arg Arg Arg
1               5                  10

<210> SEQ ID NO 27
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term palmitoyl
<220> FEATURE:
```

```
<221> NAME/KEY: MISC_FEATURE
<222> LOCATION: (1)..(20)
<223> OTHER INFORMATION: This region may encompass 0-20 residues
<220> FEATURE:
<223> OTHER INFORMATION: See specification as filed for detailed
      description of substitutions and preferred embodiments

<400> SEQUENCE: 27

Gly Gly Gly Gly Gly Gly Gly Gly Gly Gly Gly Gly Gly Gly Gly
1               5                   10                  15

Gly Gly Gly Gly Lys Lys Arg Pro Lys Pro Gly
            20                  25

<210> SEQ ID NO 28
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term octanoyl
<220> FEATURE:
<221> NAME/KEY: MISC_FEATURE
<222> LOCATION: (1)..(20)
<223> OTHER INFORMATION: This region may encompass 0-20 residues
<220> FEATURE:
<223> OTHER INFORMATION: See specification as filed for detailed
      description of substitutions and preferred embodiments

<400> SEQUENCE: 28

Gly Gly Gly Gly Gly Gly Gly Gly Gly Gly Gly Gly Gly Gly Gly
1               5                   10                  15

Gly Gly Gly Gly Lys Lys Arg Pro Lys Pro Gly
            20                  25

<210> SEQ ID NO 29
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term oleyl
<220> FEATURE:
<221> NAME/KEY: MISC_FEATURE
<222> LOCATION: (1)..(20)
<223> OTHER INFORMATION: This region may encompass 0-20 residues
<220> FEATURE:
<223> OTHER INFORMATION: See specification as filed for detailed
      description of substitutions and preferred embodiments

<400> SEQUENCE: 29

Gly Gly Gly Gly Gly Gly Gly Gly Gly Gly Gly Gly Gly Gly Gly
1               5                   10                  15

Gly Gly Gly Gly Lys Lys Arg Pro Lys Pro Gly
            20                  25

<210> SEQ ID NO 30
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (8)..(17)
<223> OTHER INFORMATION: This region may encompass 0-10 residues
```

```
<220> FEATURE:
<223> OTHER INFORMATION: See specification as filed for detailed
      description of substitutions and preferred embodiments

<400> SEQUENCE: 30

Phe Phe Phe Ile Leu Val Phe Gly Gly Gly Gly Gly Gly Gly Gly
1               5                   10                  15

Gly Lys Lys Arg Pro Lys Pro Gly
            20

<210> SEQ ID NO 31
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (7)..(16)
<223> OTHER INFORMATION: This region may encompass 0-10 residues
<220> FEATURE:
<223> OTHER INFORMATION: See specification as filed for detailed
      description of substitutions and preferred embodiments

<400> SEQUENCE: 31

Phe Leu Val Phe Phe Phe Gly Gly Gly Gly Gly Gly Gly Gly Gly
1               5                   10                  15

Lys Lys Arg Pro Lys Pro Gly
            20

<210> SEQ ID NO 32
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (8)..(17)
<223> OTHER INFORMATION: This region may encompass 0-10 residues
<220> FEATURE:
<223> OTHER INFORMATION: See specification as filed for detailed
      description of substitutions and preferred embodiments

<400> SEQUENCE: 32

Lys Lys Arg Pro Lys Pro Gly Gly Gly Gly Gly Gly Gly Gly Gly
1               5                   10                  15

Gly Phe Leu Val Phe Phe Phe
            20

<210> SEQ ID NO 33
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 10-20 residues
```

```
<400> SEQUENCE: 33

Lys Lys Lys Lys Lys Lys Lys Lys Lys Lys Lys Lys Lys Lys Lys
1               5                   10                  15
Lys Lys Lys Lys
            20
```